United States Patent [19]
Marciani

[11] Patent Number: 5,977,081
[45] Date of Patent: Nov. 2, 1999

[54] TRITERPENE SAPONIN ANALOGS HAVING ADJUVANT AND IMMUNOSTIMULATORY ACTIVITY

[75] Inventor: Dante J. Marciani, Birmingham, Ala.

[73] Assignee: Galenica Pharmaceuticals, Inc., Frederick, Md.

[21] Appl. No.: 09/081,647

[22] Filed: May 20, 1998

Related U.S. Application Data

[60] Provisional application No. 60/047,129, May 20, 1997, and provisional application No. 60/080,389, Apr. 2, 1998.

[51] Int. Cl.$^6$ ........................ A61K 31/70; A61K 31/705; C07H 15/24
[52] U.S. Cl. .......................... 514/25; 424/184.1; 514/26; 536/4.1; 536/5
[58] Field of Search .................. 514/25, 26; 536/4.1, 536/4.4, 5; 424/184.1

[56] References Cited

U.S. PATENT DOCUMENTS

| | | | |
|---|---|---|---|
| 4,235,877 | 11/1980 | Fullerton | 424/89 |
| 5,057,540 | 10/1991 | Kensil et al. | 514/25 |
| 5,273,965 | 12/1993 | Kensil et al. | 514/3 |
| 5,443,829 | 8/1995 | Kensil et al. | 424/195.1 |
| 5,508,310 | 4/1996 | Rhodes | 514/576 |
| 5,583,112 | 12/1996 | Kensil et al. | 514/25 |
| 5,650,398 | 7/1997 | Kensil et al. | 514/25 |
| 5,750,110 | 5/1998 | Prieels et al. | 424/208.1 |

FOREIGN PATENT DOCUMENTS

| | | |
|---|---|---|
| WO 90/03184 | 4/1990 | WIPO . |
| WO 93/05789 | 4/1993 | WIPO . |

OTHER PUBLICATIONS

Kensil et al. *Adv. Exp. Med. Biol.*, vol. 404: 165–172, 1996.
Pillion et al. *J. Pharm. Sci.*, vol. 85(5): 518–524, 1996.
Cleland et al. *J. Pharm. Sci.*, vol. 85(1): 22–28, 1996.
Recchia et al. *Pharm. Res.*, vol. 12(12): 1917–1923, 1995.
Higuchi, Ryuichi et al. "An Acylated Triterpenoid Saponin From *Quillaja Saponaria*," *Phytochemistry*:27(4), 1165–1168 (1988).
International Search Report for International Application No. 09/081,647, mailed Oct. 13, 1998.
Akihisa, T., et al., "The 24α– and 24β–Epimers of 24–Ethylcholesta–5,22–dien–3β–ol in Two Clerodendrum Species," *Phytochemistry* 27:1169–1172 (1988).
ApSimon, J.W., et al., "Saponins from Marine Invertebrates," in *Studies in Organic Chemistry 17: Chemistry and Biotechnology of Biologically Active Natural Products*, Proceedings of the Second International Conference, Budapest, Aug. 15–19, 1983, Szántay, C., Ed., Elsevier: Amsterdam, pp. 273–286 (1984).
Bohn, J.A., and BeMiller, J.N., "(1→3)–β–D–Glucans as biological response modifiers: a review of structure–functional activity relationships," *Carbohydrate Polymers* 28:3–14 (1995).
Bomford, R., et al., "Adjuvanticity and ISCOM formation by structurally diverse saponins," *Vaccine* 10:572–577 (1992).
Bowyer, P., et al., "Host Range of a Plant Pathogenic Fungus Determined by a Saponin Detoxifying Enzyme," *Science* 267:371–374 (1995).
Cox, J.C., and Coulter, A.R., "Adjuvants—a classification and review of their modes of action," *Vaccine* 15:248–256 (Feb. 1997).
Dalsgaard, K., "A Study of the Isolation and Characterization of the Saponin Quil A," *Acta Vet. Scand. 19* (Suppl. 69):7–40 (1978).
Dalsgaard, K., "Saponin Adjuvants. III. Isolation of a Substance from *Quillaja saponaria Molina* with Adjuvant Activity in Foot–and–Mouth Disease Vaccines," *Archiv für die gesamte Virusforschung* 44:243–254 (1974).
Higuchi, R., and Komori, T., "Structures of Compounds Derived from the Acyl Moieties of Quillajasaponin," *Phytochemistry* 26:2357–2360 (1987).
Higuchi, R., et al., "Structure of Desacylsaponins Obtained from the Bark of *Quillaja Saponaria*," *Phytochemistry* 26:229–235 (1987).
Hostettmann, K., et al., "Saponins," *Methods in Plant Biochemistry* 7:435–471 (1991).
Kensil, C.R., et al., "Structure/Function Studies on QS–21, a Unique Immunological Adjuvant from *Quillaja saponaria*," in *Saponins Used in Traditional and Modern Medicine*, Waller, G.R., and Yamasaki, K., eds., Plenum Press: New York, N.Y., pp. 165–172 (1996).
Kensil, C.R., et al., "Separation and Characterization of Saponins with Adjuvant Activity from *Quillaja saponaria* Molina Cortex," *J. Immunol. 146*:431–437 (1991).
Kensil, C.R., et al., "Structure/Function Relationship in Adjuvants from *Quillaja saponaria* Molina," *Vaccines* 92:35–40 (1992).
Lacaille–Dubois, M.A., and Wagner, H., "A review of the biological and pharmacological activities of saponins," *Phytomedicine* 2:363–386 (Mar. 1996).

(List continued on next page.)

*Primary Examiner*—Howard C. Lee
*Attorney, Agent, or Firm*—Sterne, Kessler, Goldstein & Fox P.L.L.C.

[57] ABSTRACT

The present invention is directed to novel chemical compounds in which a lipophilic moiety such as a lipid, fatty acid, polyethylene glycol or terpene is covalently attached to a non-acylated or desacylated triterpene saponin via a carboxyl group present on the 3-O-glucuronic acid of the triterpene saponin. The attachment of a lipophile moiety to the 3-O-glucuronic acid of a saponin such as Quillaja desacylsaponin, lucyoside P, or saponin from Gypsophila, Saponaria and Acanthophyllum enhances their adjuvant effects on humoral and cell mediated immunity. Additionally, the attachment of a lipophile moiety to the 3-O-glucuronic acid residue of non- or des-acylsaponin yields a saponin analog that is easier to purify, less toxic, chemically more stable, and possesses equal or better adjuvant properties than the original saponin.

50 Claims, 9 Drawing Sheets

OTHER PUBLICATIONS

Massiot, G., and Lavaud, C., "Structural Elucidation of Saponins," *Studies in Natural Products Chemistry* 15:187–224 (1995).

Newman, M.J., et al., "Saponin Adjuvant Induction of Ovalbumin–Specific CD8$^+$ Cytotoxic T Lymphocyte Responses," *J. Immunol.* 148:2357–2362 (1992).

Osbourn, A.E., et al., "Saponin Detoxification by Plant Pathogenic Fungi," in *Saponins Used in Traditional and Modern Medicine*, Waller, G.R., and Yamasaki, K., Eds., Plenum Press: New York, N.Y., pp. 547–555 (1996).

Pillion, D.J., et al., "DS–1, a Modified Quillaja Saponin, Enhances Ocular and Nasal Absorption of Insulin," *J. Pharm. Sci.* 84:1276–1279 (1995).

Price, K.R., et al., "The Chemistry and Biological Significance of Saponins in Foods and Feedingstuffs," *CRC Crit. Rev. Food Sci. Nutr.* 26:27–135 (1987).

Schöpke, Th., and Hiller, K., "Triterpenoid saponins. Part 6," *Pharmazie* 45:313–342 (1990).

Scott, M.T., et al., "Adjuvant Activity of Saponin: Antigen Localization Studies," *Int. Archs. Allergy Appl. Immun.* 77:409–412 (1985).

Sela, M., "Antigenicity: Some Molecular Aspects," *Science* 166:1365–1374 (1969).

Shibata, S., "Saponins with Biological and Pharmacological Activity," in *New Natural Products and Plant Drugs with Pharmacological, Biological or Therapeutical Activity*, Wagner, H., and Wolff, P., Eds., Springer–Verlag: Berlin, pp. 177–196 (1977).-

Quillaja

TRITERPENE SAPONIN ANALOGS HAVING ADJUVANT AND IMMUNOSTIMULATORY ACTIVITY

CROSS-REFERENCE TO RELATED APPLICATIONS

This application claims the benefit under 35 U.S.C. § 119(e) of U.S. provisional application No. 60/047,129, filed May 20, 1997 and No. 60/080,389, filed Apr. 2, 1998, both of which are entirely incorporated by reference herein.

BACKGROUND OF THE INVENTION

1. Field of the Invention

The present invention is in the field of adjuvants and immunostimulating agents. More particularly, the invention pertains to novel triterpene saponin-lipophile conjugates.

2. Related Art

Saponins are glycosidic compounds that are produced as secondary metabolites. They are widely distributed among higher plants and in some marine invertebrates of the phylum Echinodermata (ApSimon et al., *Stud. Org. Chem.* 17:273–286 (1984)). Because of their antimicrobial activity, plant saponins are effective chemical defenses against microorganisms, particularly fungi (Price et al., *CRC Crit. Rev. Food Sci. Nutr.* 26:27–135 (1987)). Saponins are responsible for the toxic properties of many marine invertebrates (ApSimon et al., *Stud. Org. Chem.* 17:273–286 (1984)). The chemical structure of saponins imparts a wide range of pharmacological and biological activities, including some potent and efficacious immunological activity. In addition, members of this family of compounds have foaming properties (an identifying characteristic), surfactant properties (which are responsible for their hemolytic activity), cholesterol-binding, fungitoxic, molluscicidal, contraceptive, growth-retarding, expectorant, antiinflammatory, analgesic, antiviral, cardiovascular, enzyme-inhibitory, and antitumor activities (Hostettmann, K., et al., *Methods Plant Biochem.* 7:435–471(1991); Lacaille-Dubois, M. A. & Wagner, H., *Phytomedicine* 2:363–386 (1996); Price, K. R., et al., *CRC Crit. Rev. Food Sci. Nutr.* 26:27–135 (1987)).

Structurally, saponins consist of any aglycone (sapogenin) attached to one or more sugar chains. In some cases saponins may be acylated with organic acids such as acetic, malonic, angelic and others (Massiot, G. & Lavaud, C., *Stud. Nat. Prod. Chem.* 15:187–224(1995)) as part of their structure. These complex structures have molecular weights ranging from 600 to more than 2,000 daltons. The asymmetric distribution of their hydrophobic (aglycone) and hydrophilic (sugar) moieties confers an amphipathic character to these compounds which is largely responsible for their detergent-like properties. Consequently, saponins can interact with the cholesterol component of animal cell membranes to form pores that may lead to membrane destruction and cell death, such as the hemolysis of blood cells.

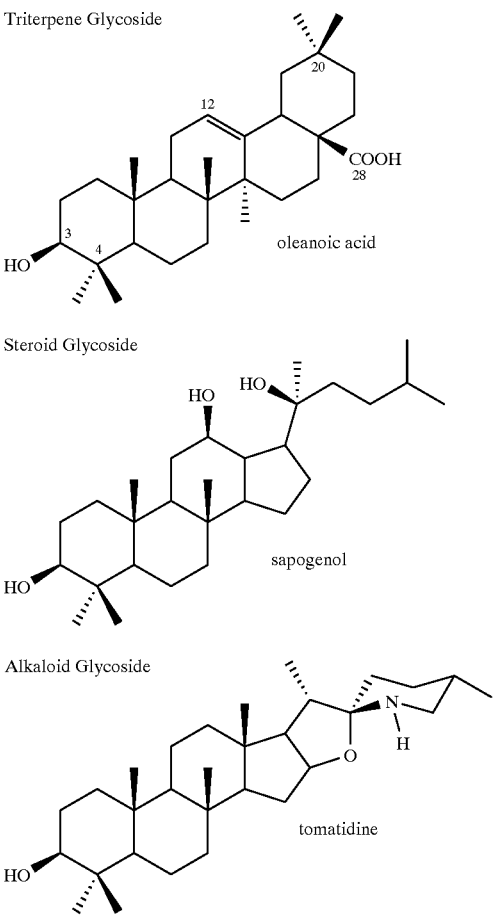

Saponins can be classified according to their aglycone composition as shown above:
1. Triterpene glycosides
2. Steroid glycosides
3. Steroid alkaloid glycosides The steroid alkaloid glycosides, or glycoalkaloids, share many physical and biological properties with steroid glycosides, but alkaloid glycosides are usually considered separately because their steroidal structure contains nitrogen. Frequently, the aglycones have methyl substituents that may be oxidized to hydroxymethyl, aldehyde or carboxyl groups; these moieties may play a role in some of the saponin's biological activities. From extensive studies of saponins, it is apparent that the triterpene saponins are not only the most predominant in nature, but also those with the most interesting biological and pharmacological properties.

Saponins have one or more linear or branched sugar chains attached to the aglycone via a glycosidic ether or ester link. In some saponins, the presence of acylated sugars has also been detected. According to the number of sugar chains attached to the aglycone, the saponins can be monodesmosidic saponins (with a single sugar chain), or bidesmosidic saponins (with two sugar chains). In the monodesmosidic saponins, the sugar chain is typically attached by a glycosidic ether linkage at the C-3 of the aglycone. In addition to the C-3 linked sugar chain, bidesmosidic saponins have a second sugar chain bound at C-28 (triterpene saponins) or at C-26 (steroid saponins) by an ester linkage. Because of the typical liability of esters, bidesmosidic saponins are readily converted into their monodesmosidic forms by mild hydrolysis (Hostettmann, K., et al., *Methods Plant Biochem.* 7:435–471 (1991)) (FIG. 2). Apparently, monodesmosidic saponins are significantly more biologically active in plants than their bidesmosidic forms. For instance, in Hedera helix the enzymatic transformation of the bidesmosidic hederasaponin C to its monodesmosidic form (α-hederin) results in a product with a high antibiotic activity (Wagner, H. & Horhammer, L., *Pharmacognosy and Phytochemistry*, Springer-Verlag, Berlin (1971)). In general, monodesmosidic saponins also tend to be more hemolytic than bidesmosidic saponins. This property appears to correlate well with their antifungal activity. Presumably, by interacting with the fungi's membrane-bound sterols, saponins alter the permeability of cell membranes leading to the organism's death (Price, K. R., et al., *CRC Crit. Rev. Food Sci. Nutr.* 26:27–135 (1987)). Consequently, the host range of plant pathogenic fungi appears to be functionally determined by their capacity to enzymatically detoxify the host organism's saponins (Bowyer, P., et al., *Science* 267:371–374 (1995)). However, the acylated quillaja saponins appear to be exceptional since their monodesmosidic forms are significantly less effective hemolytic agents than their acylated and non-acylated bidesmosidic forms (Pillion, D. J., et al., *J. Pharm. Sci.*, 84:1276–1279 (1996)). Bidesmosidic saponins most likely function as useful forms for storage and/or transport of these compounds until such time as the biologically active monodesmosidic forms are required for the plant's defense (Hostettmann, K., et al, *Methods Plant Biochem.* 7:435–471 (1991); Osbourn, A. E., et al., *Adv. Exp. Med. Biol.*, 404:547–555 (1996)). In contrast, in animals, bidesmosidic saponins may have potent biological and pharmacological activities that are completely unrelated to any aspects of plant physiology.

Saponin adjuvants from the bark of the *Quillaja saponaria* Molina tree (Quillajasaponins) are chemically and immunologically well-characterized products (Dalsgaard, K. *Arch. Gesamte Virusforsch.* 44:243 (1974); Dalsgaard, K., *Acta Vet. Scand.* 19 (*Suppl.* 69):1(1978); Higuchi, R. et al., *Phytochemistry* 26:229 (1987); ibid. 26:2357 (1987); ibid. 27:1168 (1988); Kensil, C. et al., *J. Immunol.* 146:431 (1991); Kensil et al., U.S. Pat. No. 5,057,540 (1991); Kensil et al., *Vaccines* 92:35 (1992); Bomford, R. et al., *Vaccine* 10:572 (1992); and Kensil, C. et al., U.S. Pat. No. 5,273,965 (1993)).

These saponin adjuvants are a family of closely related O-acylated triterpene glycoside structures. They have an aglycone triterpene (quillaic acid), with branched sugar chains attached to positions 3 and 23, and an aldehyde group in position 23. A unique characteristic of the Quillajasaponins is the presence of acyloil acyl moieties linked at the C-3 hydroxy group of a fucopyranose bound by an ester bond to position 28 of quillaic acid. These acyl moieties have been identified as 3,5-dihydroxy-6-methyloctanoic acid, 3,5-dihydroxy-6-methyloctanoic acid 5-O-α-L-rhamnopyranosyl-(1→2)-α-L-arabinofuranoside, and 5-O-α-L-arabinofuranoside.

Higuchi, R. et al. (*Phytochemistry* 26:229 (1987); ibid. 27:1168 (1988), and Kensil, C. et al. (U.S. Pat. No. 5,057,540, ibid., *Vaccine* 92:35 (1992) and U.S. Pat. No. 5,273,965 (1993)) have demonstrated that the 3-O-glycosidic linkage between the fucosyl residue and the acyloil acyl residue can be cleaved by mild alkaline hydrolysis to yield desacylsaponins. These desacylsaponins from Quillajasaponins are more hydrophilic than the original saponins. Apparently, deacylation of Quillajasaponins results in a significant loss of adjuvant activity, as measured by antibody production and CTl response (Kensil et al., U.S. Pat. No. 5,057,540 at column 22, lines 35 to 49; Kensil et al., *Vaccines* 92:35 (1992); and Kensil et al., U.S. Pat. No. 5,273,965, column 7, line 62).

Quillajasaponins are found as a mixture of about twenty structurally closely related triterpenoid glycosides with minimal differences between them (Higuchi, R. et al., *Phytochemistry* 26:229 (1987); ibid., 26:2357 (1987); ibid., 27:1169 (1988); Kensil et al., U.S. Pat. No. 5,057,540 (1991); Kensil et al., *Vaccines* 92:35 (1992)), making their separation difficult. Their triterpenoid group carries the aldehyde group responsible for inducing T-cell immunity, whereas their carbohydrate moieties seem to enhance humoral immunity (perhaps by interacting with lymphocyte receptors) in a fashion similar to certain polysaccharides (Bohn J. and J. BeMiller, *Carbohydrate Polymers* 28:3 (1995). In effect, PCT published application WO 90/03184 describes that saponins with their triterpenoid aldehyde reduced to alcohol are still able to induce an antibody response. Another component of quillajasaponins, the acyloil-acyl groups, likewise appear to play a role in adjuvanticity. There are also reasons to suspect that their acyloil acyl moiety, formed by a normoterpene carboxylic acid, is in part responsible for some of the toxic properties observed with several of the purified Quillajasaponins (Kensil, C. et al., *J. Immunol.* 146:431 (1991)). Thus, it would be of commercial interest to develop modified Quillajasaponins which are easier to purify, potentially less toxic, chemically more stable, and with equal or better adjuvant properties than the original saponins.

The immune system may exhibit both specific and nonspecific immunity (Klein, J., et al., *Immunology* (2nd), Blackwell Science Inc., Boston (1997)). Generally, B and T lymphocytes, which display specific receptors on their cell surface for a given antigen, produce specific immunity. The immune system may respond to different antigens in two ways: 1) humoral-mediated immunity, which includes B cell stimulation and production of antibodies or immunoglobulins [other cells are also involved in the generation of an antibody response, e.g. antigen-presenting cells (APCs; including macrophages), and helper T cells (Th1 and Th2)], and 2) cell-mediated immunity (CMI), which generally involves T cells including cytotoxic T lymphocytes (CTLs), although other cells are also involved in the generation of a CTL response (e.g., Th1 and/or Th2 cells and APCs).

Nonspecific immunity encompasses various cells and mechanisms such as phagocytosis (the engulfing of foreign particles or antigens) by macrophages or granulocytes, and natural killer (NK) cell activity, among others. Nonspecific immunity relies on mechanisms less evolutionarily advanced (e.g., phagocytosis, which is an important host defense mechanism) and does not display the acquired nature of specificity and memory, hallmarks of a specific immune response. Nonspecific immunity is more innate to vertebrate systems. In addition, cells involved in nonspecific immunity interact in important ways with B and T cells to produce an immune response. The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

A critical component of inactivated vaccines, including subunit vaccines, is an adjuvant. Adjuvants are nonimmunogenic compounds, that when administered with an antigen (either mixed with, or given prior to the administration of the antigen) enhances or modifies the immune response to that particular antigen. Thus, the humoral and/or cell-mediated immune responses are more effective when an antigen is administered with an adjuvant. Furthermore, the adjuvant may alter the quality of the immune response by affecting the subclasses (isotypes) of imnmunoglobulins produced (IgG1, IgG2, IgG3, and IgG4 for human IgGs; IgG1, IgG2a, IgG2b, and IgG3 for mouse IgGs), as well as their affinities. A response regulated by Th1 cells in mice will induce IgG I, IgG2a, IgG2b and to a lesser extent IgG3, and also will favor a CMI response to an antigen. If the IgG response to an antigen is regulated by Th2 type cells it will predominantly enhance the production of IgG1 and IgA.

Adjuvants that have been used to enhance an immune response include aluminum compounds (all generally referred to as "alum"), oil-in-water emulsions (often containing other compounds), complete Freund's adjuvant (CFA, an oil-in-water emulsion containing dried, heat-killed Mycobacterium tuberculosis organisms), and pertussis adjuvant (a saline suspension of killed *Bordatella pertussis* organisms). These adjuvants generally are thought to have their mechanism of action by causing a depot of antigen and permitting a slow release of the antigen to the immune system, and by producing nonspecific inflammation thought to be responsible for their observed activity (Cox, J. C., et al., *Vaccine* 15:248–256 (1997)). Some saponins have been shown to have different types of immune stimulating activities, including adjuvant activity. These activities have been reviewed previously (Shibata, S., *New Nat. Prod. Plant Pharmacol. Biol. Ther. Act., Proc. Int. Congr.* 1st, 177–198 (1977); Price, K. R., et al. *CRC Crit. Rev. Food Sci. Nutr.* 26:27–135 (1987); Schöpke, Th., & Hiller, K., *Pharmazie* 45:313–342 (1990); Lacaille-Dubois, M. A., et al., *Phytomedicine* 2:363–386 (1996)).

PCT published application WO 93/05789 describes conjugates in which poorly immunogenic proteins are covalently attached to purified, acylated Quillaja saponin fraction via the carboxyl group of 3-O-glucuronic acid. Addition of free quillajasaponins to these conjugates induced a higher immune response suggesting (I) that the covalently attached quillajasaponin serves as an association site for additional saponin molecules and (ii) that the adjuvant effect depends on the number of saponins associated with the protein antigen.

PCT published application WO 90/03184 describes an immunostimulating complex (ISCOM) comprising at least one lipid and at least one saponin, and that may optionally include adjuvants in addition to the saponin. These matrices are taught to be useful as immunomodulating agents and vaccines. The lipid and saponin are in a physical association, rather than covalently attached to one another. Quil A (a Quillaja saponin extract) is the preferred saponin. The reference additionally teaches that it is beneficial to add adjuvants (in addition to Quil A) to the ISCOM matrix. The reference teaches that an adjuvant lacking suitable hydrophobic properties may be modified to comprise a hydrophobic domain for incorporation into the ISCOM matrix.

Bomford, R. et al., *Vaccine* 10:572–577 (1992) teaches that lipids can be mixed with a variety of saponins to form ISCOM's. The reference teaches that Quillaja saponins, Gypsophila saponins and Saponaria saponins were the only saponins tested that were adjuvant active.

There remains a need for adjuvants that have enhanced adjuvanticity and lower toxicity.

SUMMARY OF THE INVENTION

The present invention is directed to novel chemical compounds, referred to herein as saponin-lipophile conjugates, in which (1) a non-acylated or deacylated triterpene saponin having a 3-O-glucuronic acid residue is covalently attached to:
(2) a compound having a lipophilic domain, such as a fatty acid, fatty amine, phospholipid, terpene, polyethylene glycol, among others; wherein (1) is attached to (2) via the carboxyl carbon atom present on the 3-O-glucuronic acid residue of the triterpene saponin.

The present invention is also directed to pharmaceutical and veterinary compositions comprising one or more of the saponin-lipophile conjugates, and one or more pharmaceutically acceptable diluents, carriers or excipients. These compositions may be employed as immunopotentiators in animals and humans.

The present invention is also directed to vaccines comprising one or more antigens, and a saponin-lipophile conjugate.

The present invention is also directed to enhancing the potentiation of an immune response in a mammal, comprising administering an effective amount of a saponin-lipophile conjugate to enhance the immune response of a mammal to one or more antigens.

The present invention is also directed to a method of vaccination, comprising administering one or more antigens, and a saponin-lipophile conjugate.

DETAILED DESCRIPTION OF THE PREFERRED EMBODIMENTS

Figure 1A:
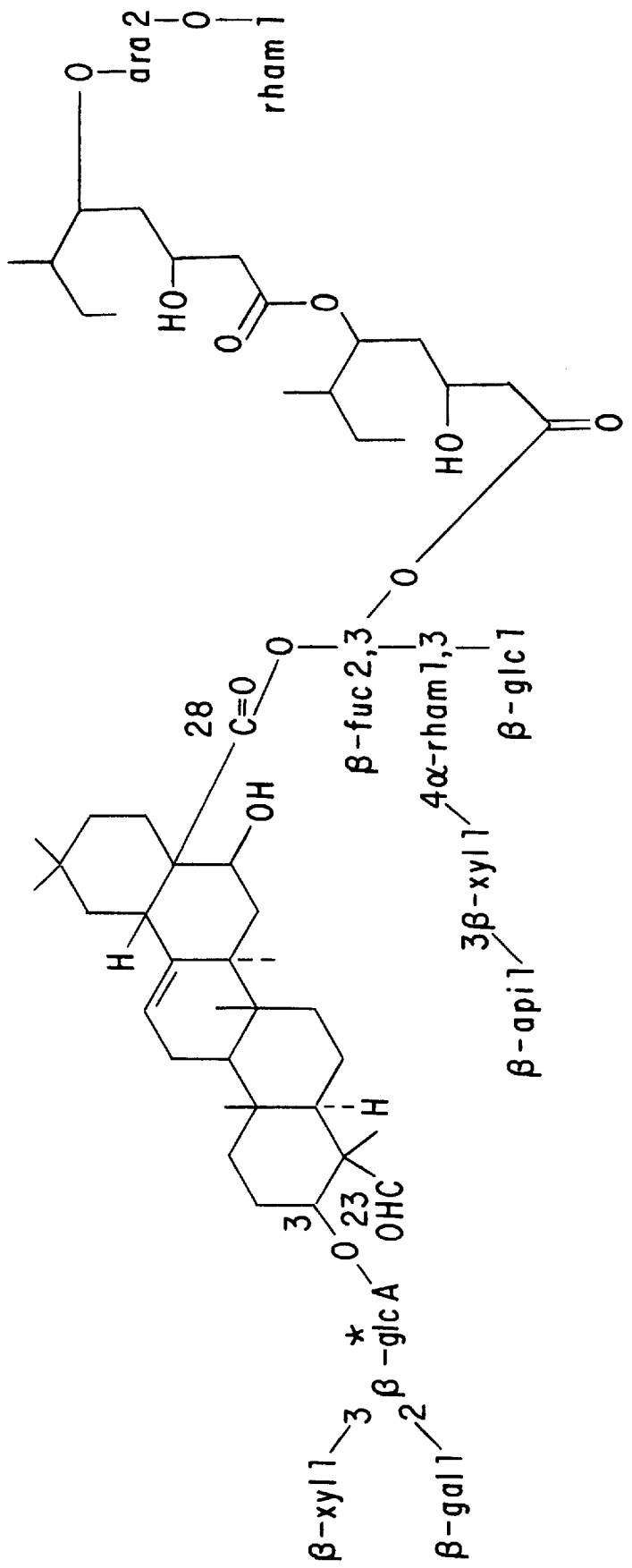
FIG. 1 illustrates representative chemical structures for saponins that are derived from Quillaja, Gypsophila and Saponaria.

The present invention is directed to novel chemical compounds, referred to herein as saponin-lipophile conjugates, comprising:

(1) a non-acylated or deacylated triterpene saponin having a 3-O-glucuronic acid residue, covalently attached to:

(2) a lipophilic moiety, for example, one or more fatty acids, fatty amines, aliphatic amines, aliphatic alcohols, aliphatic mercaptans, terpene or polyethylene glycols;

wherein (2) is attached to (1) via the carboxyl carbon atom present on the 3-O-glucuronic acid residue of the triterpene saponin, either directly or through an appropriate linking group.

The attachment of a lipophilic moiety to the 3-O-glucuronic acid of a saponin, such as *Quillaja desacylsaponins, Silene jenisseenis* Willd's desacylsaponins, lucyoside P, and Gypsophila Saponaria and *Acanthophyllum squarrosum's* saponins enhances their adjuvant effects on humoral and cell mediated immunity. Additionally, the attachment of a lipophilic moiety to the 3-O-glucuronic acid residue of nonacylated or deacylated saponin yields a saponin analog that is easier to purify, less toxic, chemically more stable, and possesses equal or better adjuvant properties than the original saponin.

In its broadest embodiment, the present invention relates to one or more modified saponins, wherein said modified saponins (a) have a triterpene aglycone core structure (such as quillaic acid, gypsogenin and others) with branched sugar chains attached to positions 3 and 28, and an aldehyde group linked or attached to position 4; (b) are either originally non-acylated, or require removal of an acyl or acyloil group that is bound to a saccharide at the 28-position of the triterpene aglycone; and (c) have a lipophilic moiety covalently attached, either directly or through a linker moiety, to the carboxylic acid of glucuronic acid at the 3-position of the triterpene aglycone.

The phrases "lipophilic moiety" and "a residue of a lipophilic molecule," as used herein, refer to a moiety that is attached by covalent interaction of a suitable functional group of one or more compounds that are non-polar or have a non-polar domain with the 3-O-glcA residue of a saponin. The lipophilic moiety can be a portion of an amphipathic compound. An amphipathic compound is a compound whose molecules contain both polar and non-polar domains. Surfactants are examples of amphipathic compounds. Surfactants typically possess a non-polar portion that is often an alkyl, aryl or terpene structure. In addition, a surfactant possesses a polar portion, that can be anionic, cationic, amphoteric or non-ionic. Examples of anionic groups are carboxylate, phosphate, sulfonate and sulfate. Examples of cationic domains are amine salts and quaternary ammonium salts. Amphoteric surfactants possess both an anionic and cationic domain. Non-ionic domains are typically derivatives of a fatty acid carboxy group and include saccharide and polyoxyethylene derivatives.

A lipophilic moiety can also comprise two or more compounds possessing non-polar domains, wherein each of the compounds has been completely bonded to a linking group, which, in turn, is covalently attached to the 3-O-glucoronic acid.

Several lipophile-containing compounds, such as aliphatic amines and alcohols, fatty acids, polyethylene glycols and terpenes, can be added to the 3-O-glcA residue of deacylsaponins and to the 3-O-glcA residue of non-acylated saponins. The lipophile may be an aliphatic or cyclic structure that can be saturated or unsaturated. By way of example, fatty acids, terpenoids, aliphatic amines, aliphatic alcohols, aliphatic mercaptans, glycosyl-fatty acids, glycolipids, phospholipids and mono- and di-acylglycerols can be covalently attached to nonacylated saponins or desacylsaponins. Attachment can be via a functional group on a lipophilic moiety that covalently reacts with either the acid moiety of the 3-glucuronic acid moiety, or an activated acid functionality at this position. Alternatively, a bifunctional linker can be employed to conjugate the lipophile to the 3-O-glcA residue of the saponin.

Useful fatty acids include $C_6$–$C_{24}$ fatty acids, preferably $C_7$–$C_{18}$ fatty acids. Examples of useful fatty acids include saturated fatty acids such as lauric, myristic, palmitic, stearic, arachidic, behenic, and lignoceric acids; and unsaturated fatty acids, such as palmitoleic, oleic, linoleic, linolenic and arachidonic acids.

Useful aliphatic amines, aliphatic alcohols and aliphatic mercaptans include amines and alcohols and mercaptans (RSH) having a straight-chained or branched, saturated or unsaturated aliphatic group having about 6 to about 24 carbon atoms, preferably 6 to 20 carbon atoms, more preferably 6 to 16 carbon atoms, and most preferably 8 to 12 carbon atoms. Examples of useful aliphatic amines include octylamine, nonylamine, decylamine, dodecylamine, hexadecylamine, sphingosine and phytosphingosine. Examples of useful aliphatic alcohols include octanol, nonanol, decanol, dodecanol, hexadecanol, chimyl alcohol and selachyl alcohol.

Useful terpenoids include retinol, retinal, bisabolol, citral, citronellal, citronellol and linalool.

Useful mono- and di-acylglycerols include mono-, and di-esterified glycerols, wherein the acyl groups include 8 to 20 carbon atoms, preferably 8 to 16 carbon atoms.

Useful polyethylene glycols have the formula H—(O—$CH_2$—$CH_2$)$_n$OH, where n, the number of ethylene oxide units, is from 4 to 14. Examples of useful polyethylene glycols include PEG 200 (n=4), PEG 400 (n=8–9), and PEG 600 (n=12–14).

Useful polyethylene glycol fatty alcohol ethers, wherein the ethylene oxide units (n) are between 1 to 8, and the alkyl group is from $C_6$ to $C_{18}$.

A side-chain with amphipathic characteristics, i.e. asymmetric distribution of hydrophilic and hydrophobic groups, facilitates (a) the formation of micelles as well as an association with antigens, and (b) the accessibility of the triterpene aldehyde to cellular receptors. It is also possible that the presence of a negatively-charged carboxyl group in such a side-chain may contribute to the repulsion of the triterpene groups, thus allowing them a greater degree of rotational freedom. This last factor would increase the accessibility of cellular receptors to the imine-forming carbonyl group.

The desacylsaponins and non-acyl saponins may be directly linked to the lipophilic moiety or may be linked via a linking group. By the term "linking group" is intended one or more bifunctional molecules that can be used to covalently couple the desacylsaponins, non-acylated saponins or mixtures thereof to the lipophilic molecule. The linker group covalently attaches to the carboxylic acid group of the 3-O-glucuronic acid moiety on the triterpene core structure, and to a suitable functional group present on the lipophilic molecule.

Non-limiting examples of linker groups which can be used to link the saponin and lipophilic molecule are alkylene diamines ($NH_2$—$CH_2$)$_n$—$NH_2$), where n is from 2 to 12; aminoalcohols (HO—($CH_2$)$_r$—$NH_2$), where r is from 2 to 12; and amino acids that are optionally carboxy-protected; ethylene and polyethylene glycols (H—(O—$CH_2$—$CH_2$)$_n$—OH, where n is 1–4) aminomercaptans and mercaptocarboxylic acids.

The present invention is useful with any saponin meeting the abovedescribed structural requirements for the reasons described herein.

The term "non-acylated saponin" or "non-acyl saponin," as employed herein, refers to a saponin that lacks an acyl or acyloil group attached to an oligosaccharide residue which itself is attached to the 28-position of the triterpene.

The term "deacylsaponin" or "deacylated saponin," as employed herein, refers to a saponin that has been modified to remove an acyl or acyloil group from an oligosaccharide residue which itself is attached to the 28-position of the triterpene.

Quillaja, Gypsophila and Saponaria are useful saponins, all having triterpene aglycones with an aldehyde group linked or attached to position 4, branched oligosaccharides linked by an ester bond in position 28, and a 3-O-glucuronic acid (3-O-glcA) that in Quillaja and Gypsophila is linked to branched oligosaccharides. Saponins from *Q. saponaria* and *S. jenisseenis* include acyl moieties, whereas saponin from Gypsophila, Saponaria, and Acanthophyllum do not include acyl moieties. Each of these non-acylated or de-acylated saponins is useful in the present invention.

Other triterpene saponin are also suitable for preparation of the lipid conjugates that are the subject of this application. These new saponin have structural characteristics similar to those saponins from *Quillaja saponaria* Molina, *Gypsophila sp.*, or *Saponaria officinalis;* i.e., they have an aldehyde and a gluconuric acid residue linked to their aglycones. These additional saponins are the bidesmosidic saponin, squarroside A, isolated from *Acanthophyllum squarrosum;* the saponin lucyoside P; and two acylated saponins isolated from *Silene jenisseensis* Willd. Following is a brief description of these compounds.

Squarroside A is a bidesmosidic saponin that contains two oligosaccharide chains linked to C-3 and C-28 of its aglycone gypsogenin. Similar to the gypsophila saponin, it has an aldehyde group linked to C-4 of the aglycone, and a glucuronic acid residue at C-3. In addition, it contains an acetylated fucose residue at C-28. It has been shown that squarroside A has immunomodulating activity as measured by an in vitro lymphoproliferative test. These apparently nonspecific immunomodulating effects were dose-dependent: a suppressive effect at concentrations in the jig range and a stimulant effect in the pg range.

Lucyoside P is a bidesmosidic saponin that has carbohydrate residue linked to C-3 and C-28 of its aglycone quillaic acid, and an aldehyde group at C-4. Lucyoside P has a glucuronic acid residue at C-3.

Two acylated saponins have been isolated from the Caryophyllacea *Silene jenisseensis*. These saponins have carbohydrates linked to C-3 and C-28 of their agylcone quillaic acid. The carbohydrate residues linked to C-3 and C-28 are glucuronic acid and fucose, respectively. The fucose residue is acylated with a p-methoxycinnamoyl group to yield trans- and cis-p-methoxycinnamoyl tritepene glycosides. Although these saponins have an aldehyde group, they have no apparent immunostimulating activity as detected by an in vitro chemiluminescence granulocyte assay. However, it is possible that the p-methoxycinnamoyl moiety is interfering with the activity of the reactive oxygen needed to produce chemiluminescence.

All of the previously described saponins have been isolated to purity. However, the acylated saponins from *Silene jenisseensis* have been obtained only as a mixture of the cis- and trans- isomeric forms. Similar to the *Q. saponaria* saponin, these acylated saponins from *Silene jenisseensis* are readily deacylated by a mild alkaline hydrolysis with ~0.2N KOH for 1 hour at room temperature. The deacylated saponin is then modified by one of the procedures described herein to yield analogs with immunostimulatory and adjuvant activities.

A preferred group of compounds for use in the present invention are desacylated quillajasaponins that have been conjugated to a lipophilic moiety via chemical reaction with the carboxylic group of the 3-O-glucuronic acid.

Thus, a preferred embodiment of the present invention relates to compounds of Formula II:

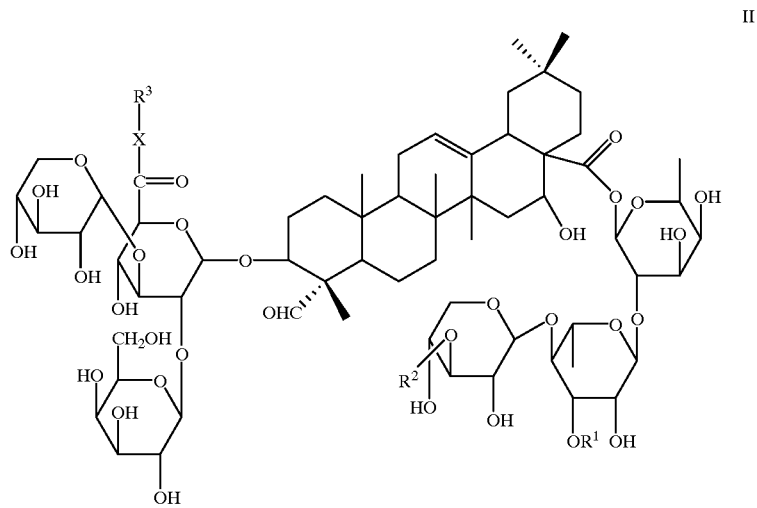

II or a pharmaceutically acceptable salt thereof; wherein
$R^1$ is glucose or hydrogen; $R^2$ is apiose or xylose, preferably apiose; X is S, O, NH or a linking group; and $R^3$ is a residue of a lipophilic molecule.

Preferred values of X include O and NH. In addition, a number of bifunctional linking groups are preferred. Useful examples include —NH—$CH_2$—$CH_2$—NH—, —NH—CH(COOH)—$CH_2$—NH—, —NH—$CH_2$—CH(COOH)—

NH—, —NH—CH$_2$—CH$_2$—CH$_2$—NH—, —O—(CH$_2$)$_r$—NH—, —S—(CH$_2$)$_r$—NH—, —S—(CH$_2$)$_r$—C(O)—, —NH—CH$_2$—C(O)—, —O—CH$_2$—CH$_2$—O—CH$_2$—CH$_2$—O—, —NH—NH—C(O)—CH$_2$—, —NH—C(CH$_3$)$_2$—C(O)—, and —NH—NH—C(O)—(CH$_2$)$_r$—C(O)—NH—N=, where r, in each instance, is from 2–5.

Preferred R$^3$ groups include the residues of fatty acids, terpenoids, aliphatic amines, aliphatic alcohols, aliphatic mercaptans, polyethylene glycols, glycosyl-fatty acids, mono- and poly- C$_2$–C$_4$ alkyleneoxy derivatives of fatty acids and fatty alcohols, glycolipids, phospholipids and mono-, di- and tri-acylglycerols that are capable of being covalently attached to the 3-O-glcA carbonyl group or to a suitable functional group on a bifunctional linker.

Useful examples of R$^3$ residues include residues of arachidonic acid, caprylic acid, retinal, decanal, carprylaldehyde, nonylamine, nonanol, dodecylamine, dodecanol, octyl glucopyranoside, lauric acid, lauryl mercaptan, sphingosine, dihydrosphingosine, 4-octylbenzaldehyde, vitamin A, and glucosamine-ricinoleic acid conjugate.

Similarly, the carboxylic acid moiety of the 3-glucuronic acid of Gypsophilia, Saponaria, and Acanthophyllum saponin, the saponin lucyoside P, and deacylated saponin from *S. jenisseenis* can be modified to provide conjugates where the acid has reacted with a suitable reagent to form an amide or ester linkage to a lipophilic moiety, either directly or via a suitable linker, as more fully described herein. The glucuronic acid is thereby converted to —C(O)—X—R$^3$, wherein X and R$^3$ are as defined above.

Saponin-lipophile conjugates that are formed by reacting Gypsophilia and Saponaria saponins are represented by Formulae III and IV, respectively:

wherein X and R$^3$ are as defined above.

Mild alkaline hydrolysis of the Quillajasaponins mixture results in breakage of the 28-O-ester bond and deacylation of the saponins, yielding two main, closely related products differing in a single glucopyranosyl residue (Higuchi, R. et al., *Phytochemistry* 26:229 (1987); ibid., 26:2357 (1987); ibid., 27:1169 (1988); Kensil et al., U.S. Pat. No. 5,057,540 (1991); Kensil et al., *Vaccines* 92:35 (1992)). These two main desacylsaponins, which can be separated by chromatographic procedures, are more hydrophilic and have less adjuvanticity than the parent saponins. However, the reduction of over twenty Quillajasaponin species to just two compounds offers a practical source of starting materials for the development and production of semisynthetic adjuvants.

Preferred starting materials include desacylated Quillajasaponins represented by Formula I:

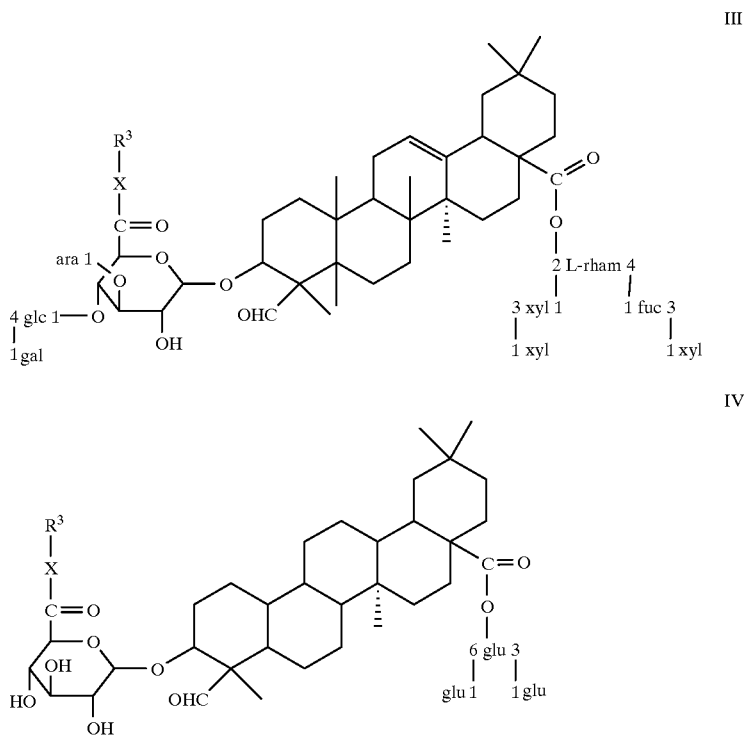

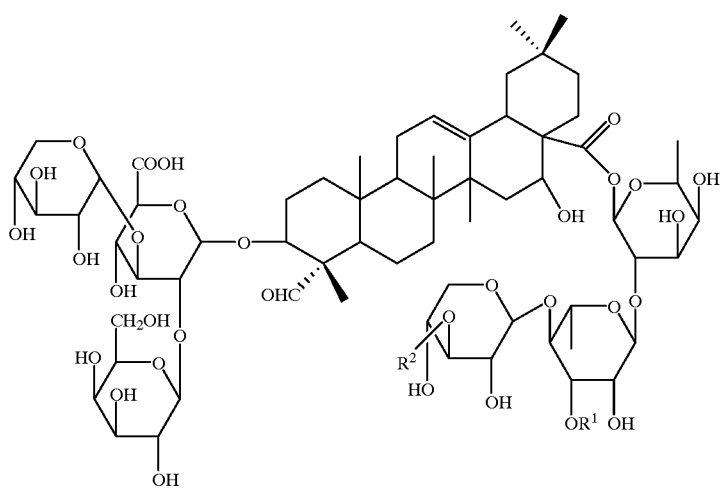

I where $R^1$ is glucose or hydrogen; and $R^2$ is apiose or xylose. In a preferred embodiment, by using the isolation procedures described herein, two desacylated Quillajasaponins, DS-1 and DS-2 can be isolated, and employed either singly or as a mixture. DS-1 refers to a compound of Formula I where $R^1$ is H; and $R^2$ is apiose or xylose. DS-2 refers to a compound of Formula I where $R^1$ is glucose; and $R^2$ is apiose or xylose.

Between 60%–70% of total desacylated quillajasaponins, representing DS-2 fraction, have a glucose residue at $R^1$. The other 30% to 40% of desacylated quillajasaponins (in which QS-21 derived product is the predominant), representing DS-1, do not have any glucose residues in their carbohydrate moiety. The extra glucose residue confers higher hydrophilicity to DS-2, which in reverse phase HPLC elutes earlier than DS-1. Most of the quillajasaponins have apiose at position $R^2$, except for a small portion of QS-21 which has xylose instead of apiose. The xylose substitute should be found mostly in the fraction DS-1. It is preferred to use the whole mixture of DS-1 and DS-2 to prepare conjugates.

Because the 3-O-glcA residue in Quillajasaponins can be modified without altering adjuvanticity, this carboxyl group offers a unique site for chemical modification of the desacylsaponins. Without wishing to be bound by theory, incorporation of a lipophilic or amphiphilic chain at the 3-O-glcA functionally substitutes for the 28-O-acyl group removed from Quillajasaponins by the alkaline hydrolysis. This modification yields neo-saponins with different physicochemical properties and adjuvanticity comparable or better than that of the original Quillajasaponins. This modification can also be used with the nonacylated saponins from *Gypsophila sp., Saponaria officinalis* and the saponin squarroside and lucyoside P to improve their adjuvant effect on the primary immunoresponse.

The desacylsaponins and non-acylated saponins can be linked to the lipophilic or amphiphilic molecule by preparing an active ester of glucuronic acid, followed by reacting the active ester with a nucleophilic functional group on the linker or lipophilic molecule. Examples of the active esters which can be used in the practice of the invention include the glucuronate of N-hydroxysuccinimide, sulfo-N-hydroxysuccinimide, hydroxybenzotriazole, and p-nitrophenol. The active esters may be prepared by reacting of the carboxy group of the saponin with an alcohol in the presence of a dehydration agent such as dicyclohexylcarbodiimide (DCC), 1-(3-dimethylaminopropyl)-3-ethylcarbodiimide (EDC), and 1-(3-dimethylaminopropyl)-3-ethylcarbodiimide methiodide (EDCI). The linker or lipophilic/amphiphilic molecule is then mixed with the activated ester in aqueous solution to give the conjugate.

Where a linker group between the saponin and the lipophilic or amphiphilic molecule is desired, the active ester of the saponin glucuronate is prepared as described above and reacted with the linker group, e.g. 2-aminoethanol, an alkylene diamine, an amino acid such as glycine, or a carboxy-protected amino acid such as glycine tert-butyl ester. If the linker contains a protected carboxy group, the protecting group is removed and the active ester of the linker is prepared (as described above). The active ester is then reacted with the lipophilic molecule to give the conjugate. Alternatively, the lipophilic molecule may be derivatized with succinic anhydride to give a lipophile-succinate conjugate which may be condensed in the presence of EDC or EDCI with a saponin-linker derivative having a free amino or hydroxyl group on the linker.

It is also possible to prepare a saponin-linker conjugate comprising a linker with a free amino group (derived from an alkylene diamine) and crosslink the free amino group with a heterobifunctional cross-linker such as sulfosuccinimidyl 4-(N-maleimidocyclohexane)-1-carboxylate which will subsequently react with the free sulfhydryl groups of lipophilic thiol compound. Examples of such linkers include amino alcohols such as 2-aminoethanol and diamines such as ethylenediamine, 1,2-propylenediamine, 1,5-pentanediamine, 1,6-hexanediamine, and the like. The lipophilic molecule can then be coupled to the linker by first forming the succinated derivative with succinic anhydride followed by condensation with the saponin-linker conjugate with DCC, EDC or EDCI.

An additional aspect of the present invention is directed to a saponin analog in which a biotinyl group has been added to the 3-O-glcA of a deacylated saponin or a non-acylated saponin, such as gypsophila and saponaria saponin. The incorporation of a biotinyl group allows for the binding of avidin or streptavidin that has been labeled with a detectable label such as a radioactive, fluorescent, paramagnetic or other type of tag or reporting group. Labeling of these compounds allows for their in vivo or in vitro detection for diagnostic purposes. For example, a FACS system can be employed for detection and determination of T-cells with cell-surface-receptors for the saponin analog. The presence of these receptors indicates which cells could potentially be stimulated by imine-forming groups to produce an immune response. Binding of the labeled avidin or streptavidin could take place either before or after the biotinylated saponin analog has bound to the cell-surface receptors.

The conjugates of the present invention, as well as useful starting materials, can be prepared according to the following procedures. Schemes to which refeence is made are presented at the end of the description section, prior to the claims.

Preparation of Starting Materials

There are two procedures which are based on mild alkaline hydrolysis to prepare the Quillaja desacylsaponins. The first procedure, described by Higuchi, R. et al. (*Phytochemistry* 26:229 (1987), fully incorporated by reference herein) starts with an alcoholic extract by Quillaja bark and the two desacylsaponins (1 and 2) are separated by chromatographic procedures (see Scheme 1). This method yields poor recoveries for both products.

A second procedure, described by Kensil, C. et al. (U.S. Pat. No. 5,057,540, fully incorporated by reference herein) starts with Quillajasaponins partially purified by ultrafiltration or by gel chromatography (Dalsgaard, *Arch. Gesamte Virusforsch.* 44:243 (1974); *Acta Vet. Scand.* 19 (*Suppl.* 69):1 (1978)). The desacylsaponins 1 (DS-1) and 2 (DS-2) are resolved by chromatographic methods. This procedure yields good recoveries for both products.

A further scheme for the preparation and isolation of desacylsaponins 1 and 2 is shown in Scheme 2.

The desacylsaponins 1 and 2 are separated prior to their chemical baa modification. In some instances, depending on the toxicity, reproducibility, efficacy, and potential regulatory issues, it would be possible to use the modified mixture of 1 and 2 as an adjuvant.

Deacylated saponin from a *S. jenisseensis* saponin can be formed by basic hydrolysis as well. See Scheme 3. The hydrolysis reaction results in removal of a trans-p-methoxycinnamoyl group.

Fatty Acid-Desacylsaponin Conjugates

Fatty acids are suitable for modifying the 3-O-glcA residue of desacylsaponins. Certain unsaturated fatty acids, such as arachidonic acid, have a series of double bonds that impose a rigid structure similar to the terpenoids, and are preferred. Other examples of preferred fatty acids include caprylic acid, caproic acid, capric acid, linoleic acid, palmitic acid, ricinoleic acid, oleic acid, palmitoleic acid, pelargonic acid, lauric acid, and eicosapentanoic acid.

Using the carbodiimide or the mixed anhydride procedures, a diamine can be coupled to a single monocarboxylic acid by an amide bond to yield a product with a free amino group. This —$NH_2$ group is then coupled to the —COOH of the desacylsaponins' 3-O-glcA using the carbodiimide method. The end product is a desacylsaponin with a fatty acid added at the 3-O-glcA residue.

The following are general protocols for forming fatty acid-desacylsaponin conjugates of the present invention.

i) Formation of the fatty acid-diamineproduct: A fatty acid, such as caprylic or arachidonic acid, can be activated to its N-hydrosuccinimide (NHS) ester by reacting with NHS and dicyclohexylcarbodiimide (DCC) in an alcohol, such as ethanol, dimethylformamide (DMF), or other convenient organic solvent. The reaction, carried out with mixing in the dark at 0° to 4° C., has for each mole of fatty acid about one mole of DCC and 1.5 to 2.0 moles of NHS. After a 4–6 hours of reaction, the precipitated dicyclohexylurea is removed by filtration, and the filtrate is added to an organic solvent containing a diamine in a 5 to 10-fold molar excess relative to the fatty acid. The diamine is preferably ethylenediamine or propylenediamine. The reaction is allowed to proceed with mixing in the dark at 0° to 4° C. for about 8 hours. The product, a diamine coupled to a single fatty acid residue by a stable amide bond, can be separated from the other reactants by selective extraction, precipitation, and/or chromatography.

Another procedure for the preparation of a fatty acid-diamine is the mixed anhydride technique: Arachidonic acid and tri-n-butylamine are dissolved in dioxane, using about 2 moles of the amine for each mole of the acid. To the cooled solution isobutylchlorocarbonate (one mole per mole of fatty acid) is added by mixing, and is reacted for 0.5 to 1 hour. This mixture is added in one portion to dioxane containing 8 to 10 times a molar excess of diamine and allowed 4 hours to react with stirring and cooling. The fatty acid-diamine can be extracted, and separated by precipitation and/or chromatography. The modified fatty acid is used for addition to the desacylsaponins.

ii) Addition of the fatty acid-diamine product to desacylsaponins:

The carboxyl of the desacylsaponins' 3-O-glcA residue is activated by the carbodiimide procedure as described above. The reaction, carried out in DMF, dioxane or other polar solvent, has for each mole of desacylsaponin about one mole of DCC and 1.5 to 2.0 moles ofNHS. The reaction is carried out in the dark at 0° to 4° C. for 4–6 hours, and the precipitated dicyclohexylurea is removed by filtration. The filtrate is added to a DMF or dioxane solution containing the fatty acid-diamine product in approximately equimolar amount with respect to the desacylsaponins; and is thereafter reacted at 25° C. for about 8 hours. The product, a conjugate consisting of a desacylsaponin having a fatty acid residue added to the 3-O-glcA residue, is separated by differential extraction, precipitation, and/or chromatography. The isolated conjugate is dissolved in water and lyophilized.

Terpenoid-Desacylsaponin Conjugates

Terpenes have structural characteristics somewhat similar to the acyloil acyl groups from Quillajasaponins. Thus, terpenes and compounds derived from terpenes (terpenoids) are suitable lipophilic molecules to conjugate to the desacylsaponins' 3-O-glcA residue. Useful terpenoids include a functional group that is capable of reacting with either the desacylsaponin or a bifunctional linker. Typical functional groups with this property that are found in terpenoids include alcohol, aldehyde and ketone functionalities. Retinal, a vitamin A aldehyde that has an important role in immunity, is an example of such a compound. A single diamine molecule is coupled to one of Retinal, yielding a Retinal with a free amino group. This product is added to the desacylated saponin using the carbodiimide method.

i) Formation of the Retinal-diamine product: To a methanolic solution containing Retinal and a 10-fold molar excess of ethylenediamine, is added sodium cyanoborohydride dissolved in methanol. The reaction is allowed to proceed for about 8 hours to reduce the reversible Schiff bases to a stable alkylamine bond. The pH is adjusted if needed with an organic acid such as acetic or trifluoroacetic acid. The Retinal-diamine product is recovered by selective solvent extraction, precipitation and/or crystallization.

ii) Addition of the Retinal-diamine product to desacylsaponins: The carboxyl of the desacylsaponins' 3-O-glcA residue is activated by the carbodiimide procedure described above. The reaction, carried out in DMF, dioxane or other suitable solvent, has for each mole of desacylsaponin 1 mole of DCC and 1.5 to 2.0 moles of NHS. After reacting in the dark at 0° to 4° C. for 4–6 hours, the precipitated dicyclohexylurea is removed by filtration. The filtrate is added to DMF or dioxane containing the Retinal-diamine product in an equimolar amount with respect to the desacylsaponins, and the mixture is allowed to react at 25° C. for about 8 hours. The product, a desacylsaponin containing a Retinal residue added to the 3-O-glcA residue, is separated by solvent extraction, precipitation, and/or chromatography. The isolated neo-saponin is dissolved in water and lyophilized.

Aliphatic amine-Desacylsaponin Conjugates

Aliphatic groups from an amine can be added to Quillaja desacylsaponins by coupling the amino group to the —COOH of the 3-O-glcA residue forming an amide bond. The carboxyl of the desacylsaponins' 3-O-glcA residue is activated by the carbodiimide procedure described above. The reaction, carried out in DMF, dioxane or other solvent, has for each mole of desacylsaponin about one mole of DCC and 1.5 to 2.0 moles of NHS. This mixture is allowed to react in the dark at 0° to 4° C. for 4–6 hours, and the precipitated dicyclohexylurea is removed by filtration. The filtrate is added to a DMF or dioxane solution containing the aliphatic amine in an equimolar amount with respect to the desacylsaponins; and allowed to react at 25° C. for about 8 hours. The product, a desacylsaponin conjugated to an aliphatic chain via the 3-O-glcA residue of the desacylsaponin, is separated by differential extraction, precipitation, and/or chromatography. The isolated conjugate is dissolved in water and lyophilized.

Glycosyl-fatty acid:desacylsaponin conjugates

Figure 1B:
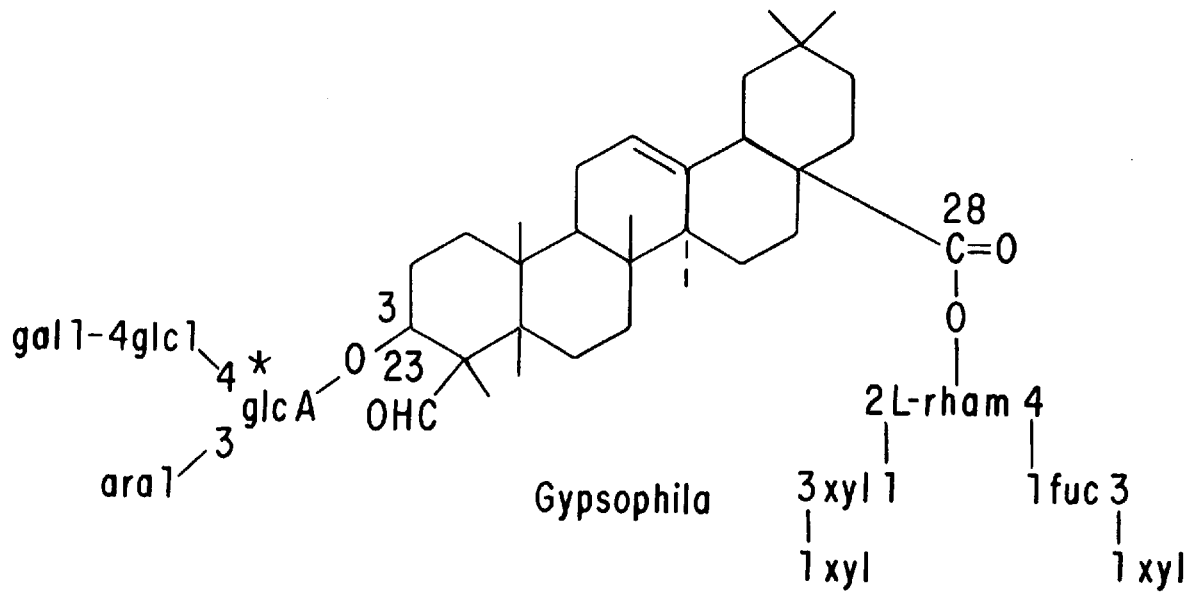
Figure 1C:
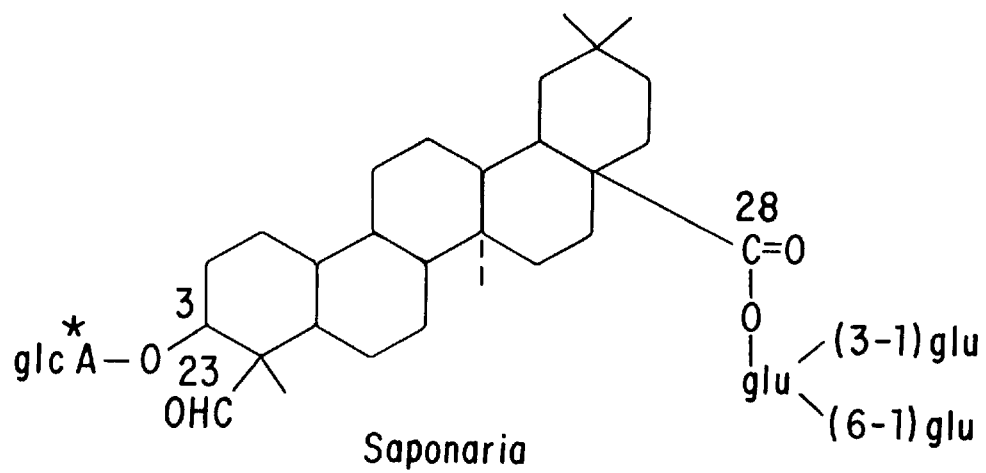

One of the acyloil acyl moieties of Quillaja saponins is linked to a disaccharide to form the structure [5-O-α-L-rhamnopyranosyl-(1→2)-α-L-arabinofuranosyl-3,5-dihydroxy-6-methyl-octanoyl]-3,5-dihydroxy-6-methyl-octanoyl]. This structure is linked by an ester bond to the C3-hydroxyl group of the fucopyranosyl residue (FIG. 1). Thus, another chemical modification is a conjugate having a glycosylated lipophile added to the 3-O-glcA residue of desacylsaponins.

i) Preparation of the glycosylated fatty acid: A fatty acid containing an alcohol group, such as the unsaturated ricinoleic acid, dissolved in dry acetone, is mixed with tosyl chloride dissolved in acetone. While stirring the reaction mixture, pyridine or triethylamine is added to neutralize the liberated HCl. The tosyl chloride converts the hydroxyl group into an active sulfonate. The sulfonate is separated from the other reactants by extraction or other adequate procedure. The active sulfonate is mixed with glucosamine in DMF, or other appropriate solvent, at pH 9.5. Sulfonates are good leaving groups that, after reaction with the glucosamine's amino group, will form stable linkages between the amine and the initial —OH group-carrying carbon. Other good leaving groups that are known in the art may be substituted for the sulfonates. The glucosamine-ricinoleic acid product is recovered by extraction, precipitation, or other procedure. This product is activated by the carbodiimide method and reacted with a diamine, in a manner equivalent to that described above for the formation of fatty acid-diamine product.

ii) Addition of glucosamine-ricinoleic acid product to desacylsaponins: The glucosamine-ricinoleic acid conjugate carrying a free amine group, introduced by reacting with a diamine using the carbodiimide method, is allowed to react with the desacylsaponin using again the carbodiimide reaction or the mixed anhydride method, both as described above for the addition of fatty acid-diamine product to desacylsaponins. The resulting conjugate is recovered by extraction, precipitation, and/or chromatography. The conjugate is dissolved in water and lyophilized. This conjugate consists of glucosamine-ricinoleic acid covalently linked to the 3-O-glcA residue of the desacylsaponin.

Synthesis of Quillajasaponin analogs having a hydrophobic/hydrophilic side-chain A side-chain with amphipathic characteristics, i.e. asymmetric distribution of hydrophilic and hydrophobic groups, facilitates (a) the formation of micelles as well as an association with antigens, and (b) the accessibility of the triterpene aldehyde to cellular receptors. It is also possible that the presence of a negatively-charged carboxyl group in such a side-chain may contribute to the repulsion of the triterpene groups, thus allowing them a greater degree of rotational freedom. This last factor would increase the accessibility of cellular receptors to the imine-forming carbonyl group.

Synthesis of a saponin analogue with a charged hydrophobic-hydrophilic side-arm i) Reaction of N-octyl-monoxyethylene with epichlorohydrin:

To 0.05 moles (9.9 ml) of N-octyl-monooxyethylene dissolved in 50 ml of dimethylformamide (DMF), add with stirring 1 equivalent (0.05 moles) of pentane-washed NaH to form an alkoxide. Add with stirring the alkoxide solution to 35 ml of DMF plus 0.2 moles (15.6 ml) of epichlorohydrin. React at <60° C., and follow the reaction by TLC. Stop the reaction by an addition of 250 ml of water. Extract the aqueous solution 3 times with 90 ml of methylene chloride reach time in order to partition the activated N-octyl-monooxyethylene. Dry the pooled organic solvent phase over magnesium sulfate, and remove the solvent in a rotary evaporator. The syrupy residue is the activated product (11). Check purity by TLC; if needed, purify by chromatography on silica gel (see Scheme 4).

ii) Addition of 2-amino-3-mercaptopropionic acid (cysteine) to n-octyl-monooxyethylene:

Prepare a fresh solution of epoxylated n-octyl-monooxyethylene by dissolving the syrupy residue (11) (<0.05 moles) in 30 ml of 0.2M potassium phosphate buffer, pH 7.8–8.4, in 50% DMF. Add (11), in small aliquots and with stirring, to 0.10 moles (12.10 gm) of L-cysteine freshly dissolved in 60 ml of the 0.2M potassium phosphate buffer, pH 7.8–8.4, in 50% DMF. If needed, adjust the pH of the cysteine solution to pH 7.8–8.4 with either 1M KOH or 1M phosphoric acid. Let react overnight at 35°–40° C. with moderate stirring under a nitrogen atmosphere. Concentrate by rotary evaporation and extract with toluene, or if soluble, with chloroform, the n-octyl-monooxyethylene cysteinyl derivative (12) (mol. wt. 351.34). The cysteine excess and other salts should remain in the aqueous phase, or precipitate in the organic solvent. Filter the organic phase, and extract twice with water to remove any potassium phosphate. Dry the organic phase over magnesium sulfate. If it is necessary to remove excess cysteine, or to change solvents (for instance: from toluene to chloroform) use chromatography on silica gel. Remove solvent by rotary evaporation, product (12) should be a syrupy residue. Check its purity by TLC on silica gel or HPLC against (11) and cysteine (see Scheme 4).

iii) Activation of quillaja saponin glucuronic acid:

To 0.4 gm (240 ~moles) of desacylated quillajasaponins dissolved in 10 ml of DMF/pyridine (60:40, v/v), add 480 μmoles (100 mg) of dicyclohexylcarbodiimide (DCC) and 480 μmoles (56 mg) of N-hydroxysuccinimide (NHS). Let the reaction proceed with mixing overnight at room temperature. (Protect from humidity). Add an additional 50 mg of DCC and 28 mg of NHS, and continue reaction for another hour. Cool the reaction to ~0°–4° C. for an hour and filter through a very fine glass filter to remove the insoluble DCC byproduct dicyclohexylurea. Remove pyridine in a rotary evaporator, and add 40 ml of cold ethyl acetate (EtOAc) to precipitate the DS-saponin:NHS derivative (13). After 1–2 hours in a freezer, collect the precipitate derivative by filtration on a fine glass filter paper, and wash the ppt on the filter paper with additional EtOAc. Product (13) can be stored under vacuum over strong dessicant (see Scheme 5).

iv) Linking of the activated DS-saponin to the hydrophobic/hydrophillic side-chain:

Dissolve the DS-saponin:NHS derivative (13) (assume 100% yield ~240 μmoles) in ~5 ml of DMF/pyridine (60:40, v/v). To the solution of (13) add 0.20 gm (~0.5 mole) of the derivative (12) dissolved in 5 ml of pyridine to yield a ~2-fold molar excess over (13). Protect from moisture and let react for 8–12 hours at room temperature to yield the saponin analog with a n-octyl-monooxyethylene cysteinyl side-chain (14). Check the reaction progress by TLC using n-butanol-pyridine-water, 3:2:1, as a solvent, and iodine or charring for detection. In a rotary evaporator remove the pyridine from the reaction mixture, add ~30 ml of cold EtOAc, and store in a freezer for 3–5 hours to precipitate (14). Collect precipitate (14) by filtering on a fine glass filter paper, and wash the precipitate with EtOAc to remove residual (12) which should be soluble in EtOAc. If needed purify (14) by chromatography on silica gel. Dissolve the saponin analog in water, and lyophilize it. Analyze (14) by HPLC, and confirm by mass spectrometry (see Scheme 6).

Synthesis of a saponin analogue with an uncharged hydrophobic-hydrophilic side-arm The synthesis of a quillajasaponin analogue having an uncharged side-arm has steps (1) and (3) in common with the synthesis described above. Steps (2) and (4) are quite similar and are described here.

Addition of ethylenediamine to n-octyl-monooyethylene

Dissolve the syrupy residue (11, prepared according to step i, above) (>0.05 moles) in 30 ml of acetonitrile 0.2N potassium carbonate. Add (11) in small aliquots and with stirring to 0.40 moles (26.7 ml) of ethylenediamine dissolved in 60 ml of 0.2M piperazine-0.2N potassium carbonate. Run the reaction at room temperature overnight with stirring. Neutralize with HCl, concentrate by rotary evaporation and dissolve the N-octyl-monooxyethylene ethylenediamine derivative (15) (mol. wt. 332.30) preferably in chloroform, otherwise in toluene. (The ethylenediamine-.HCl may be insoluble in the organic solvents, particularly if it is hydrated.) If ethylenediamine.HCl is insoluble in the organic solvent, filter through a fine glass filter, and extract the organic phase with water to remove the residual ethylenediamine. Dry the organic phase by adding dried magnesium sulfate to it. In the event that ethylenediamine cannot be removed by solvent extraction, or if the solvent needs to be changed (such as from toluene to chloroform), use chromatography on silica gel. Remove solvent in a rotary evaporator. Product should be a syrupy residue. Check its purity by TLC or HPLC against (11) and ethylenediamine (see Scheme 6).

Linking of the activated DS-saponin to the hydrophobic/hydrophilic side-chain

Dissolve the DS-saponin:NHS derivative (13, prepared according to step iii, above) (assume 100% yield ~240 μmoles) in 5 ml of DMF/pyridine (60:40, v/v). Add to (13) 0.33 gm (1 mmole) of derivative (15) dissolved in 5 ml of pyridine to yield a ~4-fold molar excess over (13). Let react for 8–12 hours at room temperature (protect from moisture) to yield the saponin analog with a N-octyl-monooxyethylene ethylenediamine side chain (16). Check progress of reaction by TLC or HPLC. In a rotary evaporator remove the pyridine from the reaction mixture, add ~30 ml of cold EtOAc, and store in a freezer for 3–5 hours to precipitate (16). Collect precipitate (16) by filtering on a fine glass filter paper, and wash the precipitate with EtOAc to remove residual (15) which should be soluble in EtOAc. If needed, purify (16) by chromatography on silica gel. Dissolve the saponin analog in water, and lyophilize it. Analyze (16) by HPLC, and confirm by mass spectrometry (see Scheme 7).

General

Toluene can be removed by rotary evaporation under reduced pressure ($bP_{760}$ 110.6° C.). DMF can be removed by rotary evaporation under reduced pressure ($bp_{39}$ 76° C., $bp_{3.7}$ 25° C.).

The N-octyl-monooxyethylene derivatives of 2,3-diaminopropionic acid and ethylendiamine should be soluble in several organic solvents, such as alcohols, ketones, and aromatic solvents, but insoluble in petroleum ether. During extraction of organic phases with water, there is a possibility of formation of emulsions due to the detergent properties of the N-octyl-monoethylene derivatives. These emulsions can be broken by either warming the suspension, or centrifuging.

Saponin analogs should be insoluble in EtOAc, alcohols such as ethanol and isopropanol and acetone.

Addition of Lipophile Groups to Related Triterpene Saponins

As indicated earlier, the non-acylated triterpenoid saponins from Gypsophila and Saponaria have a significant adjuvant effect on the secondary immunoresponse. However, different from Quillajasaponins, their effects on the primary immunoresponse are minor. It is contemplated that addition of a fatty acid moiety to these saponins will improve their adjuvanticity during the early primary immunoresponse. Strong circumstantial evidence for the proposed role of the fatty acid groups in the unique adjuvanticity of Quillajasaponins is provided by QS-7, one of these saponins (Kensil, C. et al., *J. Immunol.* 146:431 (1991); Kensil et al., U.S. Pat. No. 5,057,540 (1991)). This saponin which is very hydrophilic has (a) a retention time comparable to that of desacylated Quillaja saponins, and (b) lacks an arabinose which is the glycosyl residue associated with the Quillajasaponins' acyloil acyl moiety. These characteristics strongly suggest that QS-7 is non-acylated. This saponin also has different activities from the acylated Quillaja saponins: QS-7 is non-toxic, non-hemolytic, resembling the behavior of desacylated Quillajasaponins. While QS-7 enhances humoral immunity, its effects on antibody isotype profile are different from those observed with QS-21. These properties suggest that the acyloil moiety is responsible for the unique adjuvanticity, as well as the toxicity observed with the other Quillajasaponins. Thus, addition of an appropriate lipophile moiety to nonacylated adjuvant saponins is expected to enhance their adjuvant effects on the humoral and cell-mediated immunity, as well as limit the toxicity observed with Quillaja saponins. The latter is a crucial requirement for the successful application of these adjuvants to pediatric vaccines.

The adjuvant and immunostimulating properties of some saponins apparently have certain structural requirements, including (a) a triterpene aglycone with an aldehyde group linked or attached to position 4, and (b) branched sugar chains at positions 3 and/or 28 of the aglycone. The role of the triterpene group could be to facilitate binding to the cholesterol in cell membranes, with some subsequent involvement of the aldehyde group. Branched sugar chains appear to be important for the stimulation of humoral immunity, as indicated by the lack of adjuvanticity of quillajasaponins modified by periodate oxidation.

It has been postulated that Quillajasaponins' adjuvanticity may require a close saponin:antigen association, and that their acyl groups facilitate this association by enhancing their hydrophobicity. It has also been shown that increasing the number of quillajasaponin molecules associated with a saponin conjugated to a protein results in enhanced adjuvanticity. Apparently, the quillajasaponin molecules are being held together by hydrophobic interactions between their acyl moieties forming a micelle-like structure. Comparison of the Quillajasaponins' adjuvanticity with that of the non-acylated saponins from *Gypsophila oldhamiana* and *Saponaria officinalis* have showed somewhat similar activities. However, Quillajasaponins elicit a much higher primary immunoresponse (Bomford, R. et al., *Vaccine* 10:572 (1992)). This finding suggests that the Quillajasaponins' hydrophobic acyl moieties enhance the intrinsic adjuvant properties of their desacylsaponins.

A comparison of the structures of saponins from Quillaja, Gypsophila, and Saponaria, shows several similarities (FIG. 1). All of them have triterpene aglycones with an aldehyde group in position 23, branched oligosaccharides linked by an ester bond in position 28, and a 3-O-glucuronic acid (3-O-glcA) that in Quillaja and Gypsophila is linked to branched oligosaccharides. However, Quillajasaponins are the only ones with acyloil acyl moieties. Structure/function studies of Quillajasaponins have shown that the presence of the 23-aldehyde group, the integrity of the oligosaccharide chains, and the 28-O-acyl groups are critical for full adjuvanticity. The 3-O-glcA residue apparently can be modified without the loss of adjuvanticity. Indeed, the 3-O-glcA glycoside residue has been used to conjugate Quillajasaponins to antigens (Kensil, C. et al., *Vaccines* 92:35 (1992)). Comparison of the adjuvant activities for these saponins shows that Quillajasaponins induce a significantly better primary immunoresponse, but, that all of them induce strong secondary immunoresponses (Table I). This differential effect suggests a major role for the Quillajasaponins' acyloil acyl residues in the primary immunoresponse. The significantly lower primary immunoresponse induced by the Quillaja's desacylsaponins, as compared to those induced by its acylated saponins, provides support for this proposed role.

TABLE I

| Acylated | Quillaja sap.* | Gypsophila sap. | Saponaria sap. |
| --- | --- | --- | --- |
|  | + | − | − |
| Antibody response (log end point) | | | |
| Primary | 5.45 | 2.14 | 1.86 |
| Secondary | 8.66 | 9.13 | 6.71 |

*Quillaja saponins have an 28-O-acyloil-acyl moiety linked to fucose.

Modifications of the Gypsophila and Saponaria saponins can be carried out in a fashion similar to that described earlier for Quillaja desacylsaponins, using the carboxyl of the 3-O-glcA residue as the site for addition of new-moieties to the saponins. These neo-saponins with a new lipophile moiety in their structures should have better adjuvant properties than the original saponin molecules.

Figure 2A:
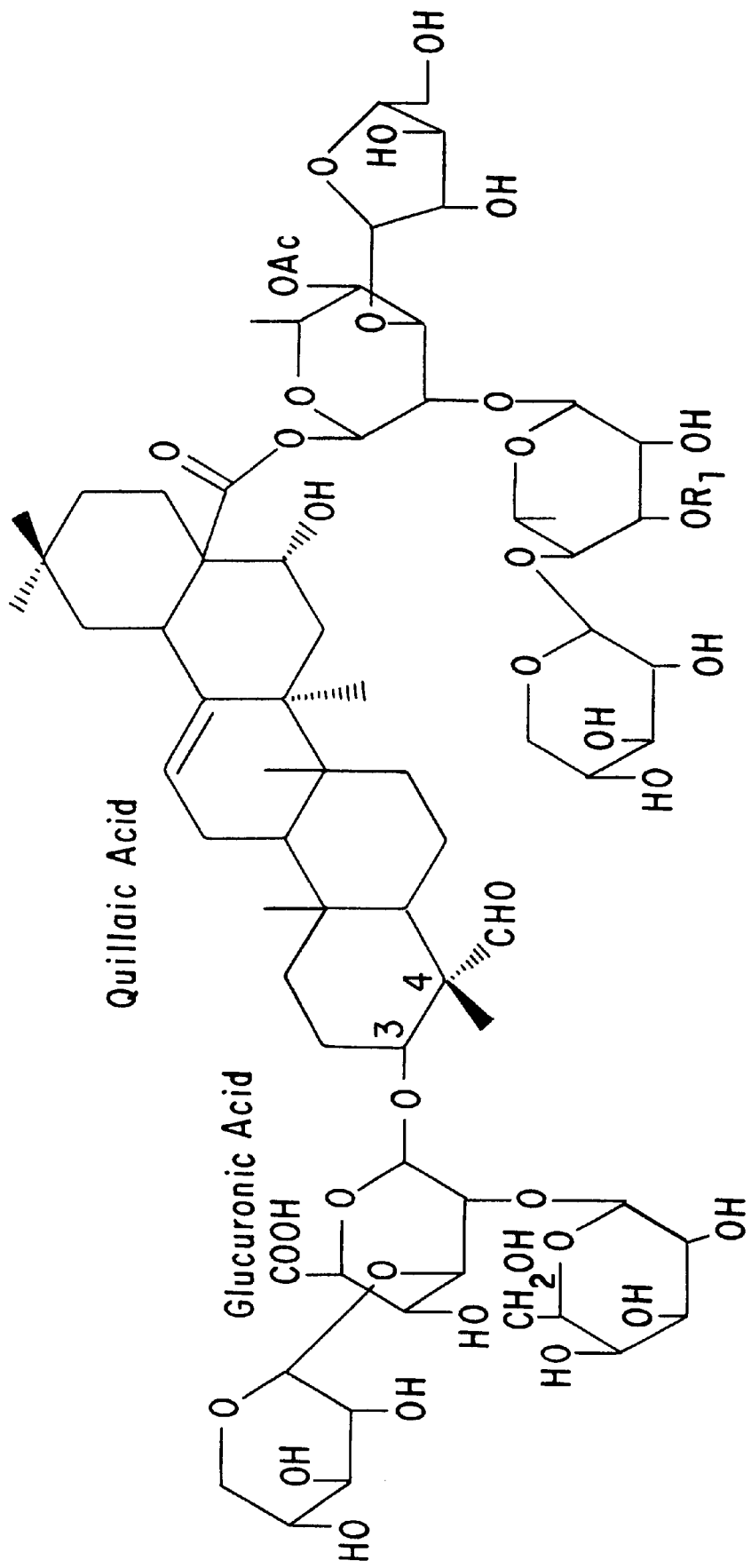
FIG. 2 illustrates representative chemical structures for (a) saponin from *Acanthophyllum squarrosum* and (b) lucyoside P.
Figure 2B:
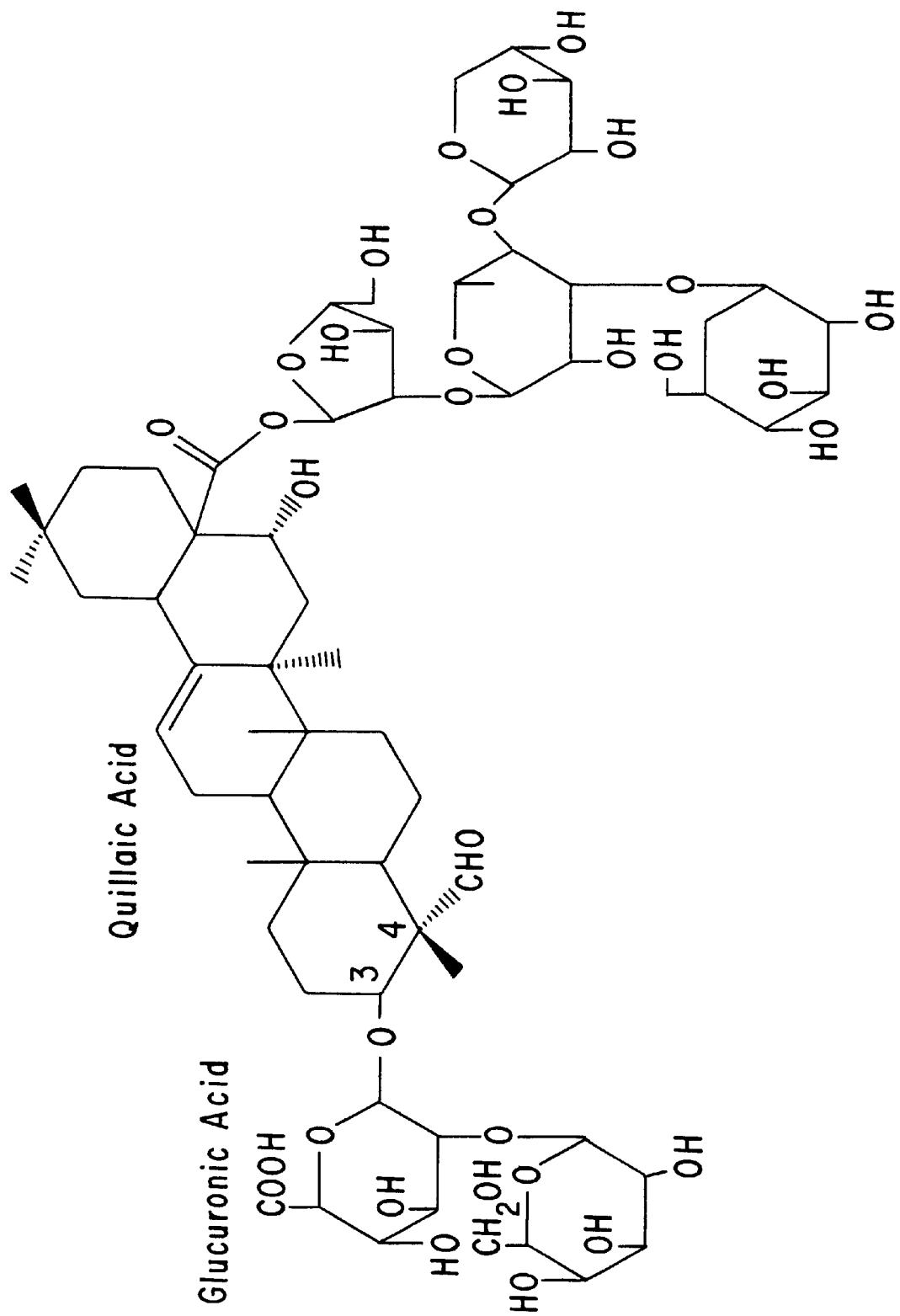
Figure 3:
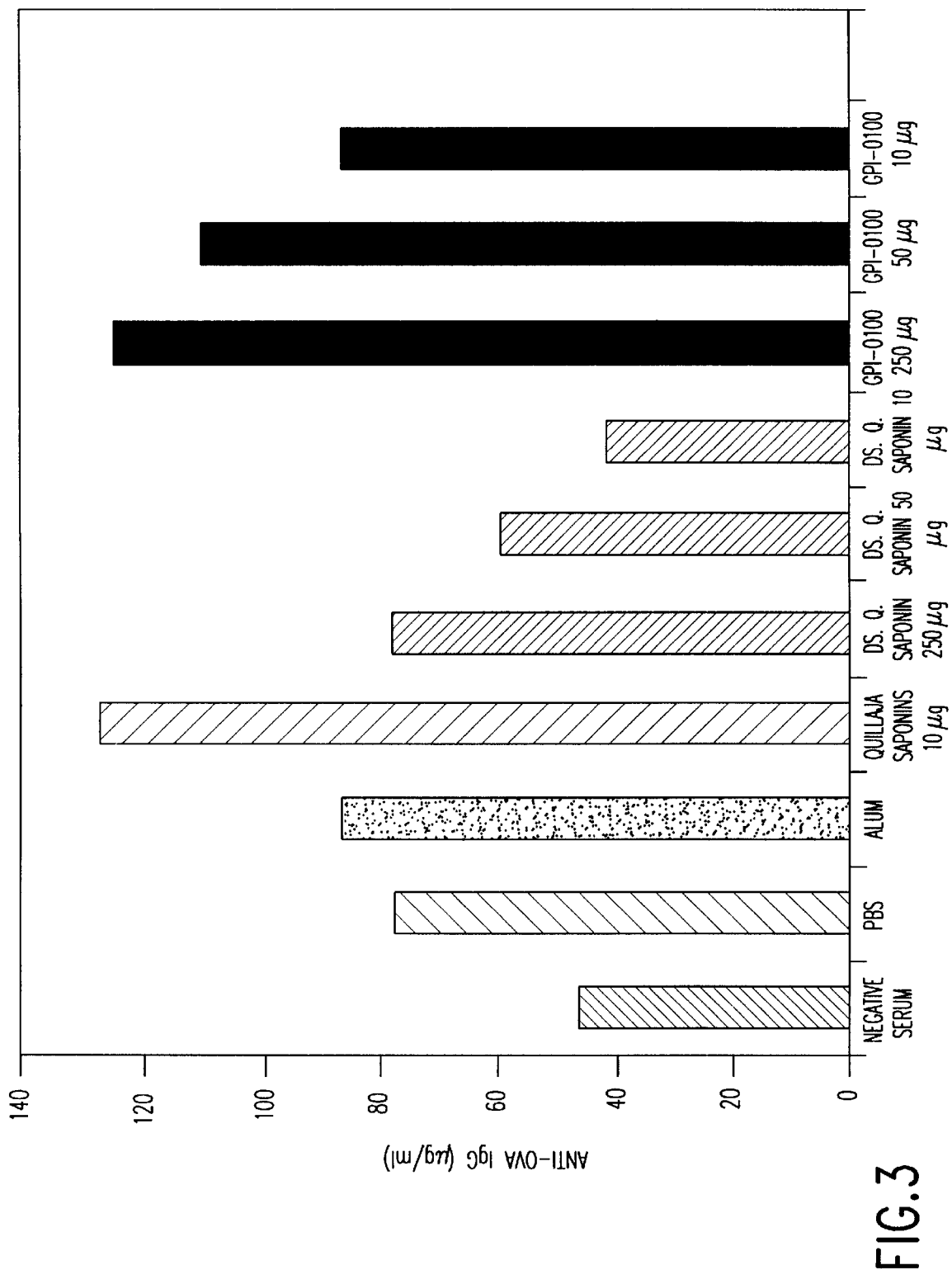
FIG. 3 demonstrates the comparison of the anti-OVA IgG primary immune response elicited by OVA alone, and in the presence of alum, quillaja saponin, and different doses of desacylated quillaja saponin, and of a quillaja saponin-lipophile conjugate (GPI-0100), Example 3 of the present invention.
Figure 4:
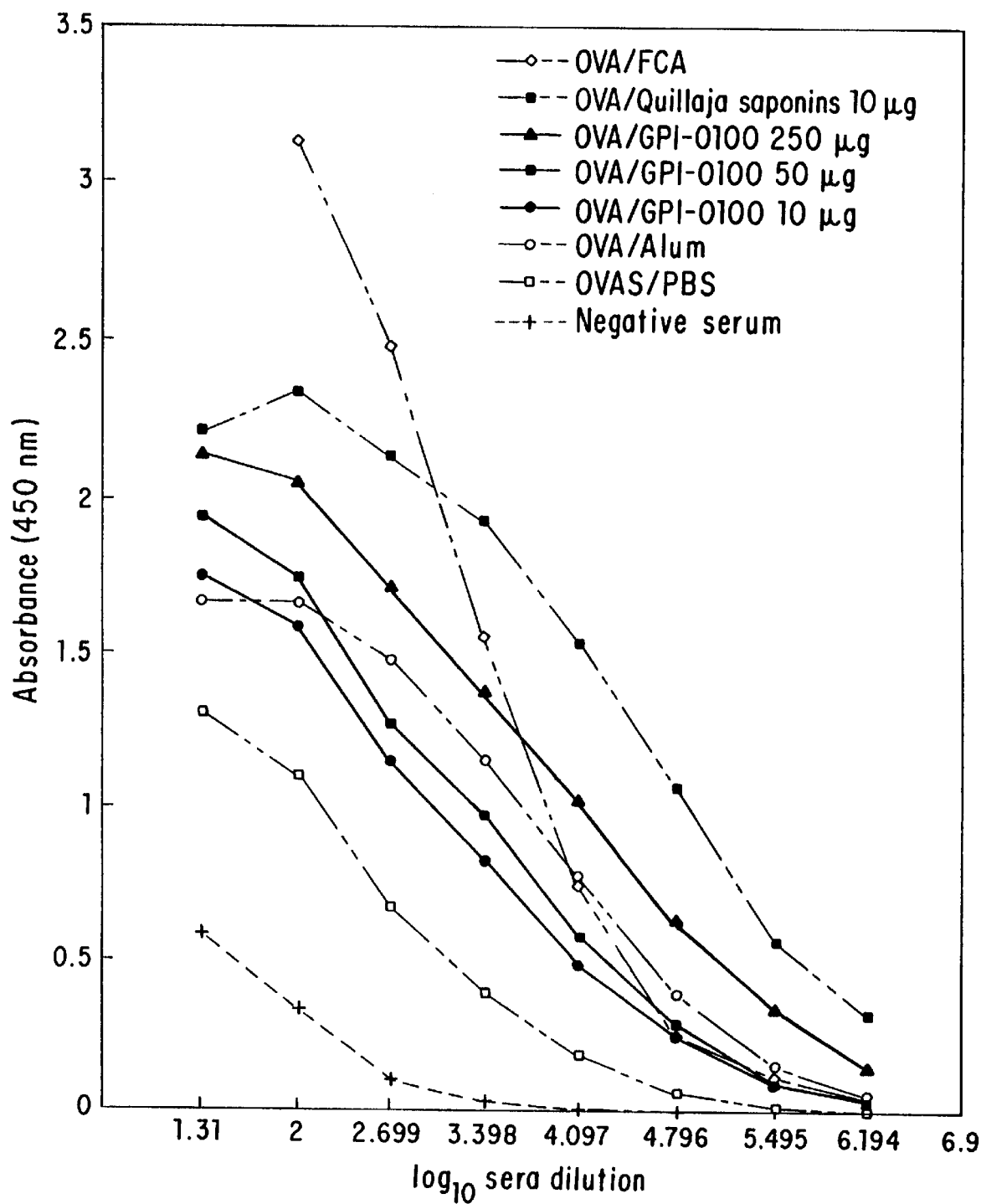
FIG. 4 shows the typical end point titers for immunization with the OVA antigen in the presence of Freund's complete adjuvant, quillaja saponin, quillaja saponin-lipophile conjugate of the present invention, alum, and OVA alone. Absorbance due to the antigen-specific antibody binding was plotted as a function of the logarithm of the sera dilution.
Figure 5:
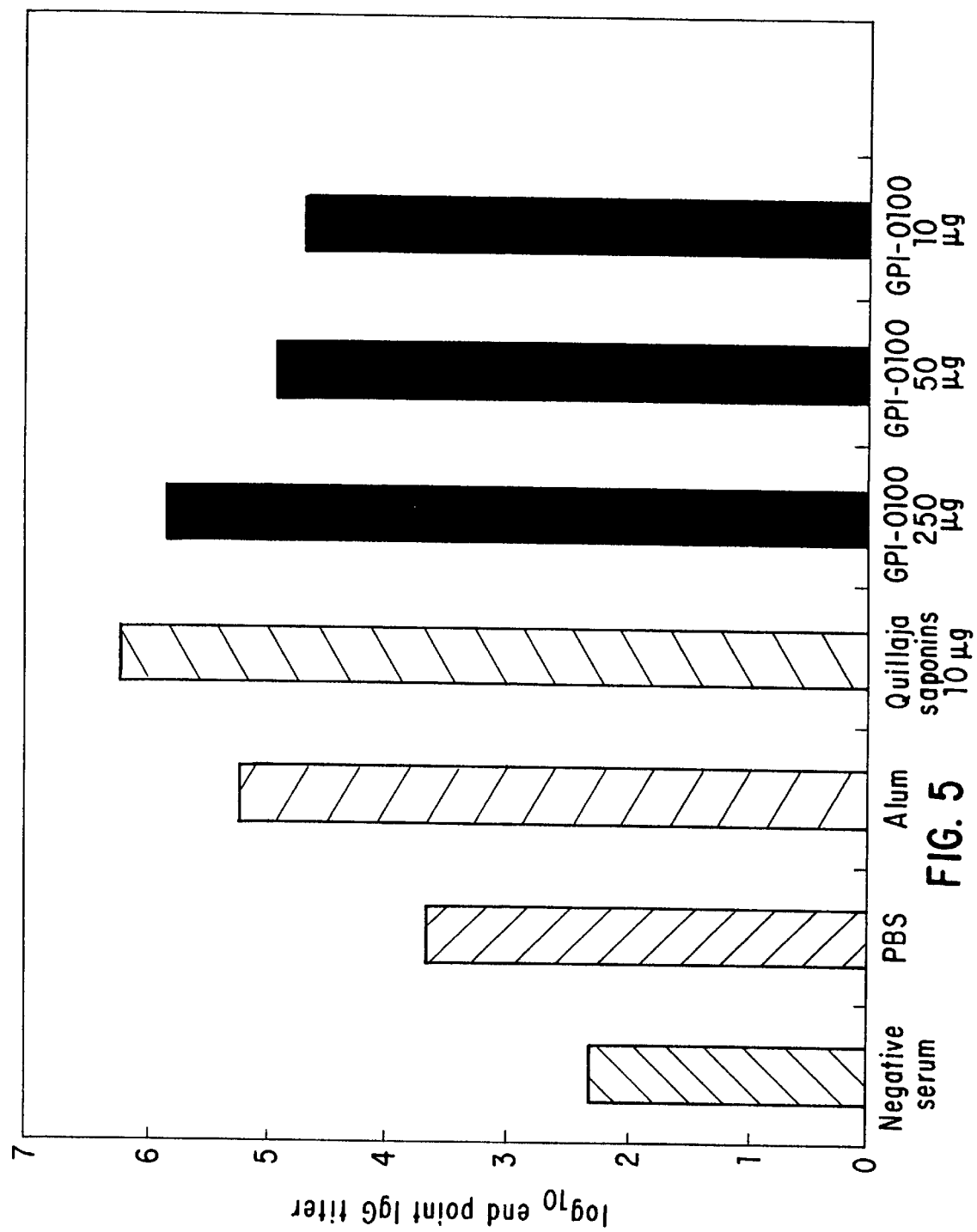
FIG. 5 demonstrates the comparison of the log end point titers for the secondary anti-OVA IgG immune response elicited by OVA alone, and in the presence of alum, quillaja saponin, and various doses of quillaja saponin-lipophile conjugate (GPI-0100).
Figure 6:
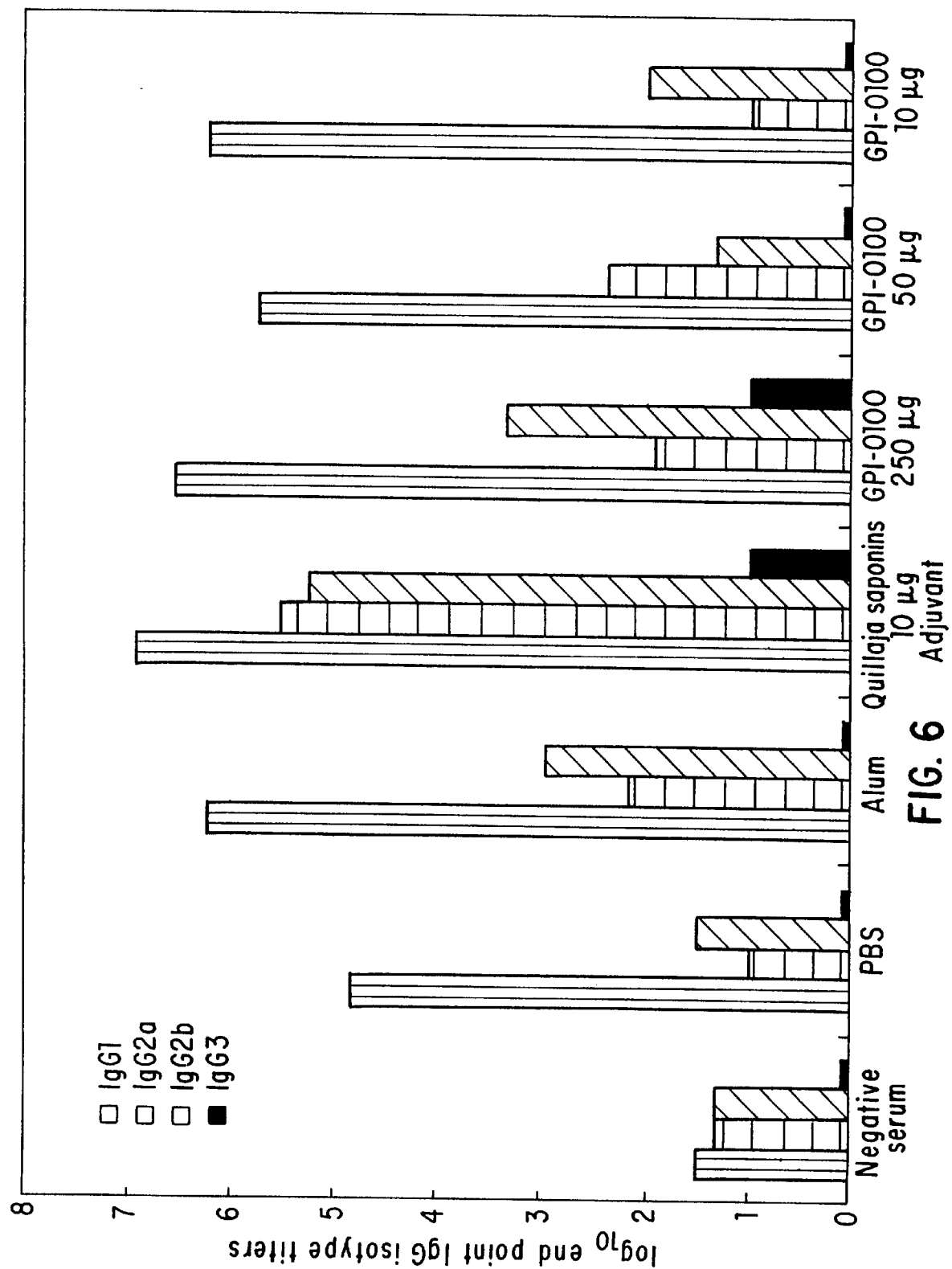
FIG. 6 shows the effects of alum, quillaja saponin, and different doses of quillaja saponin-lipophile conjugate of the present invention (GPI-0100), on the production of IgG isotypes. The log end point titers were determined using antibodies specific for each isotype.

Other non-acylated triterpene saponins, such as squarroside A, lucyoside P and *S. jenisseensis* desacylated saponin, also have the structural requirements for adjuvanticity and immunostimulating properties. For instance, it has been shown that the saponin squarroside A (FIG. 2) has immunomodulating activity, as measured by an in vitro lymphoproliferative test. Thus, these saponins can be modified by addition of lipophilic chains to their 3-O-glucuronic acid residue to produce neo-saponins with improved adjuvant properties.

Immune adjuvants are compounds which, when administered to an individual or tested in vitro, increase the immune response to an antigen in a subject to which the antigen is administered, or enhance certain activities of cells from the immune system. Some antigens are weakly immunogenic when administered alone or are toxic to a subject at concentrations that evoke useful immune responses in a subject. An immune adjuvant can enhance the immune response of the subject to the antigen by making the antigen more strongly immunogenic. The adjuvant effect can also result in the ability to administer a lower dose of antigen to achieve a useful immune response in a subject.

Immune adjuvants can modify or "immunomodulate" the cytokine network, up-regulating the immune response. Concomitant with this immunomodulation there is also a selection of which T-cell, Th1 or Th2, will mount this immune response. Th1 responses will elicit complement fixing antibodies and strong delayed-type hypersensitivity reactions associated with IL-2, IL-12, and γ-interferon. Induction of CTL response appears to be associated with a TH1 response. Th2 responses are associated with high levels of IgE, and the cytokines IL-4, IL-5, IL-6 and IL-10. The aldehyde-containing saponins induce a strong Th1 response. However, some of their analogs may induce a Th2 response.

The immunogen-inducing activity of compounds and compositions of the present invention can be determined by a number of known methods. The increase in titer of antibody against a particular antigen upon administration of a composition of the present invention can be used to measure immunogenic activity. (Dalsgaard, K. *Acta Veterinia Scandinavica* 69:1–40 (1978)). One method requires injecting CD-1 mice intradermally with a test composition that includes one or more exogenous antigens. Sera is harvested from mice two weeks later and tested by ELISA for anti-immunogen antibody.

Compositions of the invention are useful as vaccines to induce active immunity towards antigens in subjects. Any animal that may experience the beneficial effects of the compositions of the present invention within the scope of subjects that may be treated. The subjects are preferably mammals, and more preferably humans.

Saponin-lipophile conjugates of the present invention can be employed as a sole adjuvant, or alternatively, can be administered together with non-saponin adjuvants. Such non-saponin adjuvants useful with the present invention include oil adjuvants (for example, Freund's Complete and Incomplete), liposomes, mineral salts (for example, AlK$(SO_4)_2$, AlNa$(SO_4)_2$, AlNH$_4$(SO$_4$), silica, alum, Al(OH)$_3$, Ca$_3$(PO$_4$)$_2$, kaolin, and carbon), polynucleotides (for example, poly IC and poly AU acids), polymers (for example, non-ionic block polymers, polyphosphazenes, cyanoacrylates, polymerase-(DL-lactide-co-glycoside), among others, and certain natural substances (for example, lipid A and its derivatives, wax D from *Mycobacterium tuberculosis*, as well as substances found in *Corynebacterium parvum*, *Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the non-saponin adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenylmethane-3,3'-dicarboxylic acid and 4-nitro-2-aminobenzoic acid (See Sela, M., *Science* 166:1365–1374 (1969)) or glycolipids, lipids or carbohydrates.

The chemically modified saponins of the present invention exhibit adjuvant effects when administered over a wide range of dosages and a wide range of ratios to one or more particular antigens being administered.

The chemically modified saponins can be administered either individually or admixed with other substantially pure adjuvants to achieve an enhancement of immune response to an antigen. The chemically modified saponins can be a substantially pure modified saponin, or can be in the form of a mixture of chemically modified saponins.

The saponin lipophile conjugates of the present invention can be utilized to enhance the immune response to one or more antigens. Typical antigens suitable for the immune-response provoking compositions of the present invention include antigens derived from any of the following: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, or tuberculosis; or protozoans, such as *Babeosis bovis* or Plasmodium. The antigen can be proteins, peptides, polysaccharides, or mixtures thereof. The proteins and peptides may be purified from a natural source, synthesized by means of solid phase synthesis, or may be obtained means of recombinant genetics. The antigen may comprise a protein fragment comprising one or more immunogenic regions of the molecule.

The saponin conjugates of the present invention can be utilized to enhance the immune response against antigens produced by the use of DNA vaccines. The DNA sequences in these vaccines coding for the antigen can be either "naked" or contained in a delivery system, such as liposomes. Typical vaccines using this approach are viral vaccines, such as influenza, herpes, cytomegalovirus, HIV-1, HTLV-1, FIV, cancer vaccines, and parasitic vaccines. The saponin conjugates can be administered together with the DNA or at an earlier and/or later time than the DNA administration.

Cancer cells often have distinctive antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, quillajasaponin and saponin-lipophile conjugates can be utilized. Triterpenoid saponin adjuvants containing an aldehyde work by reacting with amino groups of the receptor protein(s) present on certain T-cells, and forming Schiff bases. As a result of this reaction, exogenous proteins are allowed to enter the pathway for processing endogenous antigens, leading to the production of cytolytic or cytotoxic T cells (CTL). This unique adjuvant effect induces the production of antigen specific CTLs which seek and destroy those tumor cells carrying on their surface the tumor antigen(s) used for immunization. The saponin conjugates of the present invention can also be used with carbohydrate tumor antigens, such as gangliosides, the Thomsen-Friedenreich (T) antigen, and others.

The saponin conjugates of the present invention can also be administered alone to potentiate the immune system for treatment of chronic infectious diseases, especially in immune compromised patients. Examples of infectious diseases for which conjugates of the present invention can be employed for therapeutic or prophylactic treatment are described in U.S. Pat. No. 5, 508,310. Potentiation of the immune system by saponin conjugates can also be useful as a preventative measure to limit the risks of nosocomial and/or post-surgery infections.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the saponin/antigen conjugates may be administered over a wide range of dosages and a wide range of ratios to the antigen being administered. The initial dose may be followed up with a booster dosage after a period of about four weeks to enhance the immunogenic response. Further booster dosages may also be administered.

The saponin-lipophile conjugates of the present invention may be employed in such forms as capsules, liquid solutions, emulsions, suspensions or elixirs for oral administration, or sterile liquid forms such as solutions, emulsions or suspensions. Any inert carrier is preferably used, such as saline, or phosphate-buffered saline, or any such carrier in which the compounds used in the method of the present invention have suitable solubility properties for use in the methods of the present invention.

The saponin-lipophile conjugates of the present invention can be employed in association with liposomes, wherein the saponin can be in one or both of the bilayers of the liposome, loosely-associated with lipid material in a liposome preparation (where the conjugates are not within a bilayer, but otherwise associated with lipids), in some instances, entrapped within the bilayers of the liposomes. See, for example, U.S. Pat. No. 4,235,877 to Fullerton.

The invention also provides for a kit for the immunization of an individual comprising a carrier compartmentalized to receive in close confinement therein one or more container means wherein a first container contains a saponin-lipophile conjugate of the invention. The kit may also include at least one other container means which contains a saponin adjuvant or other adjuvant as described herein.

Addition of Biotinyl group to Related Triterpene Saponins

As earlier indicated, biotinylated saponin analogs are useful reagents for identifying and determining which cells of the immune system have receptors capable of reacting with imine-forming saponins. These saponins (such as those from quillaja, gypsophila, and saponaria) replace the co-stimulatory ligand B7.1 that is expressed on APCs and react with CD28 receptor on T-cells. Upon costimulation with B7.1 or an imine-forming saponin adjuvant, T-cells are activated to form antigen-specific CTLS. The use of these tagged saponin analogs allows for the determination of the progress of the immune response process by qualitatively or quantitatively measuring the presence of T-cells that have cell surface receptors that can bind to desacylated or non-acylated saponins.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Preparation of Quillaja Desacylsaponins (4)

The required triterpene saponin starting materials can be obtained from commercial preparations of *Quillaja saponaria* Molina saponins, which are acylated. By way of example, two kinds of commercial preparations can be used:

(a) Quillaja saponins (practical grade, obtained from Fisher Scientific), contain approximately 25% (w/w) of saponins and 75% (w/w) of water-soluble contaminants, i.e., oligosaccharides, tannins, etc.; and (b) Dialyzed Quillaja saponins or Quil A (obtained from Accurate Chemicals or Sigma Chemical Co.) are >80% (w/w) saponins with a methanol insoluble contaminant(s).

Practical grade Quillaja saponins can be further purified as follows:

A. Practical grade saponin preparation (1) is dissolved in water to a concentration of 20–25% (w/v) and the pH is adjusted to about 4 with 1N acetic acid to form a cloudy solution. The cloudy solution is poured into a standard dialysis sack and dialyzed against 3–4 changes of 25–50 volumes of water for 24 hours. Water is changed every 4–8 hours of dialysis. The dialysate is then lyophilized, yielding a white colored preparation. After dialysis, the saponin preparation (2) contains a contaminant (perhaps pigments or tannins) which is insoluble in methanol. Yield: ±25% of the initial weight of the practical grade saponin preparation, which represents about 95% (w/w) of the original saponins.

B. One gm of dry saponin preparation (2) is extracted with 50 ml of methanol at 60° C. for 20–25 minutes. The suspension is filtered and undissolved material is re-extracted with 30 ml of methanol at 60° C. for 20–25 minutes. The clear methanolic filtrates are pooled and brought to dryness with a rotoevaporator. The methanol-extracted saponin preparation (3) is free of methanol-insoluble contaminant(s). Yields are up to 70% of preparation (2).

The acyl groups of Quillaja saponins are removed by mild alkaline hydrolysis to yield four distinct desacylsaponins (two being isomers), plus 3,5-dihydroxy-6-methyloctanoic acid, and 3,5-dihydroxy-6-methyloctanoic acid 5-O-α-L-rhamnopyranosyl-(1→2)-α-arabinofuranoside. By way of example, the following alkaline hydrolysis methods are useful in preparing these desacylated saponins (4).

(i) Methanol extracted saponins (3) (60 mg/ml) are boiled with 6% $Na_2CO_3$ in 50% methanol for 1 hour, and the reaction mixture neutralized with Dowex 50W-X8 $H^+$ (a synthetic, strongly-acidic cation exchanger that is a sulfonated polystyrene-divinylbenzene resin) and filtered. The filtrate is concentrated with a rotoevaporator, and partitioned between ethyl acetate and water. The aqueous phase will include most of the desacylsaponins, whereas the organic EtOAc phase will contain most of the octanoic acids. The EtOAc is removed from the aqueous phase by passing nitrogen gas or using a rotoevaporator, and the aqueous desacylsaponin solution (4) is lyophilized.

(ii) Methanol extracted saponins (3, 0.1 gm) are resuspended in 3 ml of 90% n-propanol. This suspension/solution is adjusted to 0.5N NaOH by addition of a 5N NaOH stock solution and mixed for 2 hours at room temperature (20°–25° C.). The suspension is centrifuged 5 minutes at 50×g to yield a lightly colored supernatant, which is discarded, and a brownish grainy precipitate. The precipitate is washed three times by resuspending it with 3 ml of 90% n-propanol and centrifuging at 50×g. The resulting pellet of desacylsaponins (4) is redissolved in 3 ml water and lyophilized.

Alternatively, methanol extracted saponins (3) are dissolved in water to form a solution having 20 mg/ml saponins and the solution is adjusted to a final concentration of 0.15M triethylamine, pH 12. After one hour at 40°–50° C., the alkaline hydrolysis is terminated by adding acetic acid to pH 7.0. The reaction mixture is extracted with ethyl acetate to remove triethylamine and some hydrolysis products. The desacylsaponins (4) should remain in the aqueous phase. Another procedure is to dissolve (3) (10 mg/ml) in concentrated ammonia, stir the solution for 5 hours at room temperature, and remove the ammonia under a stream of nitrogen. The aqueous solution is extracted with 80 ml of ethylacetate, and the organic phase is discarded. The aqueous phase containing the desacylsaponins is frozen and lyophilized.

EXAMPLE 2

Purification of Saponin From Gypsophyla Sp.

A 5% solution of crude gypsophyla saponin in 10 mM acetic acid is dialyzed in a dialysis sack having a molecular weight cut-off of ~2,000 Daltons against 20 volumes of 10 mM acetic acid at 4° C. The acetic acid solution is changed two times after 4 hours. (This step removes polysaccharide and some small molecular weight contaminants). The dialized solution is concentrated in a rotoevaporator and lyophilized. One gram of the dialized gypsophyla saponin is extracted twice with 50 ml of pure methanol (MeOH) at room temperature for 24 hours each and filtered. If there is un-dissolved material, extract once with 50 ml of MeOH:water (40/60) at room temperature, and filter to remove insoluble matter. Filtrates are pooled and concentrated at ~40° C. in a rotoevaporator to yield a syrupy saponin extract (I). Dissolve the extract in water to yield a 5% saponin solution, and extract this solution twice with 0.5 volume of ethyl acetate. The aqueous phase is submitted to chromatography on Fractogel TSK HW-40F, eluting with a gradient of 0 to 50% (v/v) of MeOH in water containing 0.05M $Na_2CO_3$. Samples were analyzed by TLC on silica gel using n-butanol:acetic acid:water (4/1/5) as a solvent, and the saponin visualized with the Liebermann:Burchard reaction. Alternatively, the saponin from (I) can be precipitated by adding 5 volumes of ethyl acetate, and fractionated by silica gel chromatography using chloroform:MeOH:water (64:40:8) as a solvent. Analogs of gypsophyla saponin can be prepared using the same procedures developed for the desacylated quillaja saponins.

EXAMPLE 3

Addition of Aliphatic Amine Via Carboxyl Group of Glucuronic Acid

A $C_6$–$C_{20}$ aliphatic amine, preferably a $C_9$ or $C_{12}$ aliphatic amine, can be added to the carboxyl of the glucuronic acid residue of desacylsaponins (4) to yield conjugated desacylsaponins (5) using the carbodiimide method. Either DCC (dicyclohexylcarbodiimide), or water-soluble EDC (1-ethyl- 3-(3-dimethylaminopropyl)carbodiimide, with or without NHS (N-hydroxysuccinimide) or water-soluble sulfo-NHS, can be used. The reaction is carried out in organic solvents, such as dioxane, DMF (dimethylformamide), THF (tetrahydrofuran), DMSO (dimethylsulfoxide), alcohols and pyridine, alone or in mixtures anhydrous or with water. The presence of water is dictated by the solubility properties of the Quillaja desacylsaponins, which can be soluble in 50% methanol, 50% n-propanol, aqueous DMSO, and DMF, as well as anhydrous THF or dioxane, and other solvents with similar properties.

(i) One-step method (a) To 100 mg (60 μmoles) of desacylsaponins (4) dissolved in 1 ml of 50% n-propanol, is added 1 ml of a 0.6M dodecylamine solution (600 μmoles) in 50% n-propanol. The pH is then adjusted to between 5 and 7 with 3N phosphoric acid. 600 μmoles of dry EDC (95 mg) is stirred into the resulting solution and mixed for 6–8 hours (0° C. to 10° C.). An additional 300 μmoles (47 mg) of EDC is added, and the reaction is allowed to proceed overnight at 0° C. to 10° C. The reaction can be stopped by removing the free alkylamine with a Dowex 50 type resin. (The resin may also remove the acyl urea from EDC.) The resin is removed by filtration. The filtrate containing the conjugated desacylsaponins (5) is mixed with 5 volumes of n-propanol to precipitate (5). The precipitate is collected, dissolved in water, dialyzed and lyophilized.

(b) If the desacylsaponins are soluble in anhydrous pyridine, alone or with anhydrous THF, the reaction can be carried out with DCC. 100 mg of (4) (60 μmoles) are dissolved in pyridine and/or THF, using no less than 1 ml but no more than 5 ml. 1 ml of a 0.3M dodecylamine solution (300 μmoles) in pyridine and/or THF is thereafter added to the reaction mixture, followed by 300 μmoles of dry DCC. The mixture is allowed to react with mixing overnight at 0° C. to 10° C. During the reaction, insoluble dicyclohexylurea is formed; this is removed by centrifugation. The supernatant containing the conjugated desacylsaponins (5) is diluted with 10 volumes of EtOAc to precipitate (5). The EtOAc containing the free alkyl amine, residual DCC, and the pyridine and/or THF is discarded. Precipitate is washed with EtOAc, dissolved in water and re-extracted with EtOAc before removing the EtOAc and lyophilizing.

(ii) Two-step method (a) To 100 mg (60 μmoles) of desacylsaponins (4) dissolved in 1 ml of 50% n-propanol is added 0.2 ml of a 0.6M dodecylamine solution (120 μmoles) in 50% n-propanol. The pH of the mixture is adjusted to pH 5–7 with 3N phosphoric acid (carboxylic acids are to be avoided). 120 μmoles of dry EDC (10 mg) and 120 μmoles sulfo-NHS (26 mg) are added to the reaction mixture with stirring and the reaction is allowed to proceed overnight at 0° C. to 10° C. Five volumes of n-propanol are added to precipitate the conjugated desacylsaponins (5). The precipitate is collected, dissolved in water, dialyzed and lyophilized.

(b) If desacylsaponins are soluble in anhydrous pyridine alone or mixed with anhydrous THF, the reaction can be carried out with DCC. 100 mg of (4) (60 μmoles) are dissolved in pyridine and/or THF, using no less than 1 ml but no more than 5 ml of solvent. 0.4 ml of a 0.3M dodecylamine solution (120 μmoles) in pyridine and/or THF is added to the desacylsaponin solution, followed by 120 μmoles of dry DCC and 120 μmoles of dry NHS. The mixture is allowed to react with mixing overnight at 0° C. to 10° C. Insoluble dicyclohexylurea is formed, which is removed by centrifugation. The supernatant containing the conjugated desacylsaponins (5) is diluted with 10 volumes of EtOAc to precipitate (5) and to remove the free alkyl amine, residual DCC, and NHS. The precipitate is dissolved in water and extracted with EtOAc before concentration with a rotoevaporator and lyophilization. Modification is confirmed by mass spectra.

Another preferred embodiment of the invention is one in which two or more hydrophobic chains are introduced at the carboxyl group of the 3-O-glucuronic acid residue of a desacylated or non-acylated saponin. This addition of multiple lipophilic chains can be made using different chemical approaches, including those described below. Preferably, a molecule that includes two or three lipophilic side-chains is covalently attached to the 3-O-glucuronic acid, either directly or via a bifunctional linker.

EXAMPLE 4

Addition of phosphatidylethanolamine dipalmitoyl to desacylsaponin

To 0.35 gm (210 mmoles) of desacylsaponins (4) dissolved in 3 ml of anhydrous DMF/pyridine (60:40, v/v) at room temperature, is added 280 mmoles of phosphatidylethanolamine fatty acid derivative (dipalmitoyl, distearoyl, and others) in DMF/pyridine. To this reaction mixture is added with mixing 400–600 mmoles of dry DCC (0.08–0.125 gm) and 400 mmoles of dry NHS (0.05 gm) and allowed to react with mixing for 12–16 hours at rt. The reaction mixture is cooled to 4° C. for an hour and filtered to remove insoluble dicyclohexylurea, a DCC byproduct. To the filtrate containing the conjugated desacylsaponins is added 10 volumes of cold ethanol to precipitate the conjugated desacylsaponins and to remove residual DCC, NHS, and free phosphatidylethanolamine fatty acid derivative. After 2–4 hours at 0°–4° C., the precipitated saponin conjugate is collected by filtration. The precipitate is washed on the filter paper with 10–20 ml of ethyl acetate. The precipitated saponin conjugates are then dissolved in 10 ml. of water, and this solution is extracted with 1 volume of ethyl acetate. The ethyl acetate is removed from the aqueous solution using a rotoevaporator, and the sample is lyophilized.

EXAMPLE 5

Addition of L-2,4-diaminobutyric Acid Dimyristoyl to Desacylsaponin

To 0.63 gm (2.5 mmoles) of myristoyl chloride dissolved in 25 ml of acetonitrile, is added 2.10 gm (11 mmoles) of 2,4-diaminobutyric dihydrochloride, plus 2.00 gm potassium carbonate. The mixture is reacted with stirring for 12–16 hours at 65° C. The reaction mixture is thereafter dried under reduced pressure, and the residue is dissolved in ethyl acetate, extracted with water, and again extracted with water saturated with magnesium sulfate. The organic phase is dried over anhydrous magnesium sulfate. The magnesium sulfate is removed by filtration. The filtrate is dissolved under reduced pressure, and the purity of the compound is checked by silica gel TLC. If needed, the dimyristoyl derivative is purified by chromatography on silica gel.

To 0.40 gm, (240 mmoles) of desacylsaponins (4) dissolved in 5 ml of anhydrous DMF/pyridine (60:40, v/v) at room temperature is added 2 ml of DMF/pryidine containing 0.23 gm of dimyristoyl derivative. Thereafter, 480–720 mmoles of dry DCC (0.10–0.15 gm) and 480 mmoles of dry NHS (~0.06 gm) are added with mixing, and allowed to react with mixing for 12–16 hours at room temperature. The reaction mixture is cooled to 4° C. for an hour and filtered to remove insoluble dicyclohexylurea, a DCC byproduct. To the filtrate containing the conjugated desacylsaponins is added 10 volumes of cold ethanol to precipitate the conjugated desacylsaponins and to remove residual DCC, NHS, and free dimyristoyl derivative. After 2–4 hours at 0°–4° C., the precipitated saponin conjugate is collected by filtration. The precipitate is washed on the filter paper with 20–30 ml of ethyl acetate. The precipitated saponin conjugate is dissolved in 20 ml of water, and the solution is extracted with 1 volume of ethyl acetate. The ethyl acetate is removed from the aqueous solution using a rotoevaporator and is lyophilized. The sample purity is checked by silica gel TLC. If necessary, the conjugated desacylsaponin can be purified by chromatography on silica gel.

EXAMPLE 6

Addition of Citric Acid-Tripalmitoyl to Desacylsaponin

To 0.50 gm (2.5 mmoles) of citric acid dissolved in 20 ml acetonitrile or pyridine is added with mixing 3.60 gm (15 mmoles) of 1-hexadecylamine. To this solution is added 35 mmoles of dry DCC (7.20 gm) and 35 mmoles of NHS (4.00 gm), and allowed to react overnight at rt. The reaction mixture is cooled to 4° C. for an hour and is filtered to remove insoluble dicyclohexylurea. Solvent is removed under reduced pressure in a rotoevaporator. The dry residue is dissolved in alcohol and the residual alkylamine is removed with a strongly acidic resin (Dowex 50). The purity of the product is checked by silica gel TLC. If necessary, the product is purified by chromatography on silica gel. The citric acid-tripalmitoyl derivative (1.87 gm, 2 mmoles) is dissolved in 20 ml of acetonitrile, and 2.5 mmoles of 1,1'-carbonyldiimidizole (CDI) (0.40 gm) is added and the mixture is allowed to react for 4 hours at rt under anhydrous conditions. A 5-fold excess of ethylene diamine (10 mmoles~0.65 ml) is then added to the reaction mixture and allowed to react for another 2–3 hours at rt. Thereafter, 10% water is added to destroy residual CDI, and solvent is removed under reduced pressure. The reaction products are dissolved in a suitable solvent, e.g. methanol or chloroform, and purified by silica gel chromatography. Fractions containing the aminated citric acid-tripalmitoyl derivative (M.W.~1019.7) are pooled, and solvent is removed under reduced pressure.

The desacylated saponin conjugate is prepared by reacting in pyridine/DMF (40:60, v/v) 1 mole of desacylsaponin with 1.5 moles of the aminated citric acid-tripalmitoyl derivative using the DCC/NHS method described before. After filtration to remove the insoluble dicyclohexylurea, the conjugated saponin is precipitated with several volumes of ethyl acetate, redissolved in water and lyophilized.

EXAMPLE 7

Preparation of Saponin Analogs Having Steroid or Triterpenoid Moieties

The disclosed invention is not limited to linear hydrophobic chains as the lipophilic moiety. Non-aromatic and aromatic cyclic and heterocyclic compounds, such as triterpenoids and steroids can also be employed as the lipophilic moiety. As an example, the preparation of a steroid derivative is described here. To 2 mmoles of deoxycholic acid (0.79 gm) in 10 ml of pyridine, is added with mixing 10 mmoles (0.67 ml) of ethylenediamine, followed by 4 mmoles of dry DCC (0.82 gm) and 4 mmoles of NHS (0.50 gm). The mixture is allowed to react overnight at 25° C. The reaction is then cooled and the insoluble DCC byproduct is filtered, and solvent is removed under reduced pressure. The products are dissolved in a small volume of chloroform-methanol (3:2, v/v) or similar solvent, and the aminated product is separated from the ethylenediamine by chromatography on silica gel. The solvent is removed under reduced pressure.

The desacylated saponin conjugate is prepared by reacting 1 mole of desacylsaponin with 2 moles of the aminated deoxycholic acid derivative using the DCC/NHS method described above. The conjugated saponin is precipitated with alcohol, re-dissolved in water and lyophilized.

EXAMPLE 8

Testing for Adjuvant Effect Using Ovalbumin (OVA) as Antigen

Adjuvant effect can be assessed by increase in antigen-specific antibody titers due to addition of potential adjuvant in the immunization formulation. Increased titers result from increased antibody concentrations and/or increased antigen/antibody affinity. Adjuvant effects of saponins have previously been measured by increase in titer of neutralizing antibodies to foot-and-mouth disease vaccines in guinea pigs (Dalsgaard, K., *Archiv. fur die gesamte Virusforschung* 44:243–254 91974)), increase in titer of precipitating antibodies to BSA (as measured by radial immunodifflusion) in guinea pigs vaccinated with BSA/saponin mixtures (Dalsgaard, K., *Acta Veterinaria Scandinavica* 69:1–40 (1978)), as well as by the increase in titer of anti-keyhole limpet hemocyanin (KLH) antibody (measured by ELISA) in mice immunized with KLH/saponin (Scott et al. *Int. Archs. Allergy appl. Immun.* 77:409–412 (1985)).

Assessment of adjuvant effect can be determined by increase in anti-OVA antibody following immunization with OVA/saponins, OVA/desacylated saponin s or OVA/saponin analogs, compared with immunization with OVA in the absence of saponin. The adjuvant activity in the saponin conjugate fraction is measured as follows: CD2F 1 mice (8–10 weeks old) are immunized intradermally with the following formulation: 20 $\mu$g OVA (Sigma) and adjuvant of the present invention or quillajasaponin (at doses ranging from 10–2500 $\mu$g), or quillaja saponin (at a dose of 10 $\mu$g) in 200 $\mu$l PBS. The two immunizations are given at two-week intervals. Control mice are injected with either PBS or PBS with OVA, plus 200 $\mu$g of aluminum hydroxide. Sera is harvested two weeks post-immunization. Anti-OVA antibody is determined by ELISA: Immulon II plates were coated overnight at 4° C. with 100 $\mu$l of an OVA solution (10 mg/ml in PBS) in rows, A, C, E, and G. Plates are washed twice with PBS. Nonspecific binding is prevented by incubating for 1.5 h at 37° C. with 100 $\mu$l diluent (2% casein acid hydrolysate (Oxoid, w/v) in PBS) per well in all wells. Plates are washed four times with 0.05% Tween 20 surfactant in distilled water. Sera at dilutions of 1:20, 1:100, 1:500, 1:2500, 1:12,500, 1:62,500, 1:312,500 and 1:1,562,500 is incubated in rows A+B, C+D, E+F and G+H, respectively (100 $\mu$l/well) for 1 h at room temperature. Plates are washed as described above. Boehringer-Mannheim horse radish peroxidase conjugate goat anti-mouse antibody (1/5000 in 5% OVA in diluent) is incubated for 30 min at room temperature (100 $\mu$l per well, all wells). Plates are washed as described above. The extent of peroxidase reaction is determined by reaction with 2,2'-azido-bis(3-ethylbenzthiazoline)-6-sulfonate (30 minute reaction at room temperature, absorbance measured at 450 nm) or with 3,3',5,5'-tetramethylbenzidine (10 min. reaction of nonspecific antibody binding to the total antibody binding is removed by subtraction of the absorbance of the antigen-negative well from the absorbance of the antigen-positive well for each sera dilution. The IgG produced during the primary immune response is determined by interpolating the absorbance values obtained with a 1:20 serum dilution in a calibration curve. The calibration curve is constructed using known amounts of an anti-OVA IgG monoclonal antibody which is processed simultaneously with the immune sera samples. The secondary anti-OVA IgG immune response is determined from the end-point titers as follows: the absorbance due to antigen-specific binding is plotted as a function of the logarithm of the serum dilution, and the end-point titer is estimated from the serum dilution yielding an absorbance of 0.25. End-point titers of 3.6 or less are obtained with sera from immunizations without an adjuvant, and end point titers near or higher than 5.0 with different adjuvants. Dialyzed *Quillaja saponaria* Molina saponins at an adjuvant does of 10 μg increases titers by almost 2 orders of magnitude compared to OVA in PBS. The primary immune response from immunizations with OVA plus desacylated quillajasaponins yields IgG levels lower that those elicited by OVA in PBS.

A conjugate as prepared in Example 3 (dodecylamine conjugated to desacylated quillaja saponin) was tested for adjuvanticity at doses of 10, 50 and 250 μg. The conjugate demonstrated a good dose-dependent adjuvant effect on the production of anti-OVA IgG during the primary and secondary immune response (FIGS. 3, 4, 5, 6). This conjugate yields end-point titers approaching those induced by quillaja saponin, i.e. 4.70 to 5.85. As opposed to quillajasaponins, this conjugate preferentially stimulates the production of IgG1. No negative side effects were observed with this conjugate in the dose range tested: 10 to 250 μg.

EXAMPLE 9

Testing for Adjuvant Effect On T-Cell Immunity Using OVA as Antigen

In many viral vaccines, and likely in cancer vaccines, the adjuvant used with the protein antigens should elicit a strong specific cell-mediated immunity (CMI) or T-cell immune response with production of cytotoxic T lymphocytes (CTL). Presently, quillajasaponins are the only adjuvants capable of eliciting T-cell immunity (Newman et al., *J. Immuno.* 148:2357 (1992)). The other adjuvants, including muramyl dipeptides, glucans, immune modulators such as IL-2, and others, are only capable of stimulating a humoral immune response against exogenous proteins (Cod, J. C., and Coulter, A. R., *Vaccine* 15:248 (1997)), which would be of little value in the case of cancer and some viral vaccines. Desacylation of quillajasaponins results in non-toxic products, but, with no adjuvant activity, as measured by antibody production (Kensil et al., *Vaccines* 92:35 (1992)) and CTL response (Kensil et al., in *Saponins Used in Traditional and Modern Medicine;* Kamasaki, K., Waller, G. R., Eds. Plenum, N.Y., in press). Because of their stimulation of humoral and T-cell immunity, as well as negligible toxicity, the semi-synthetic analogs or saponin-lipophile conjugates of the present invention are suitable for the preparation of viral or cancer vaccines. T-cell immunity induced by these adjuvants can be assayed in vitro by (i) blast transformation, which measures the proliferation response of sensitized T cells to antigens, or (ii) measurement of the enhancement of CTL priming to a protein antigen.

Figure 7:
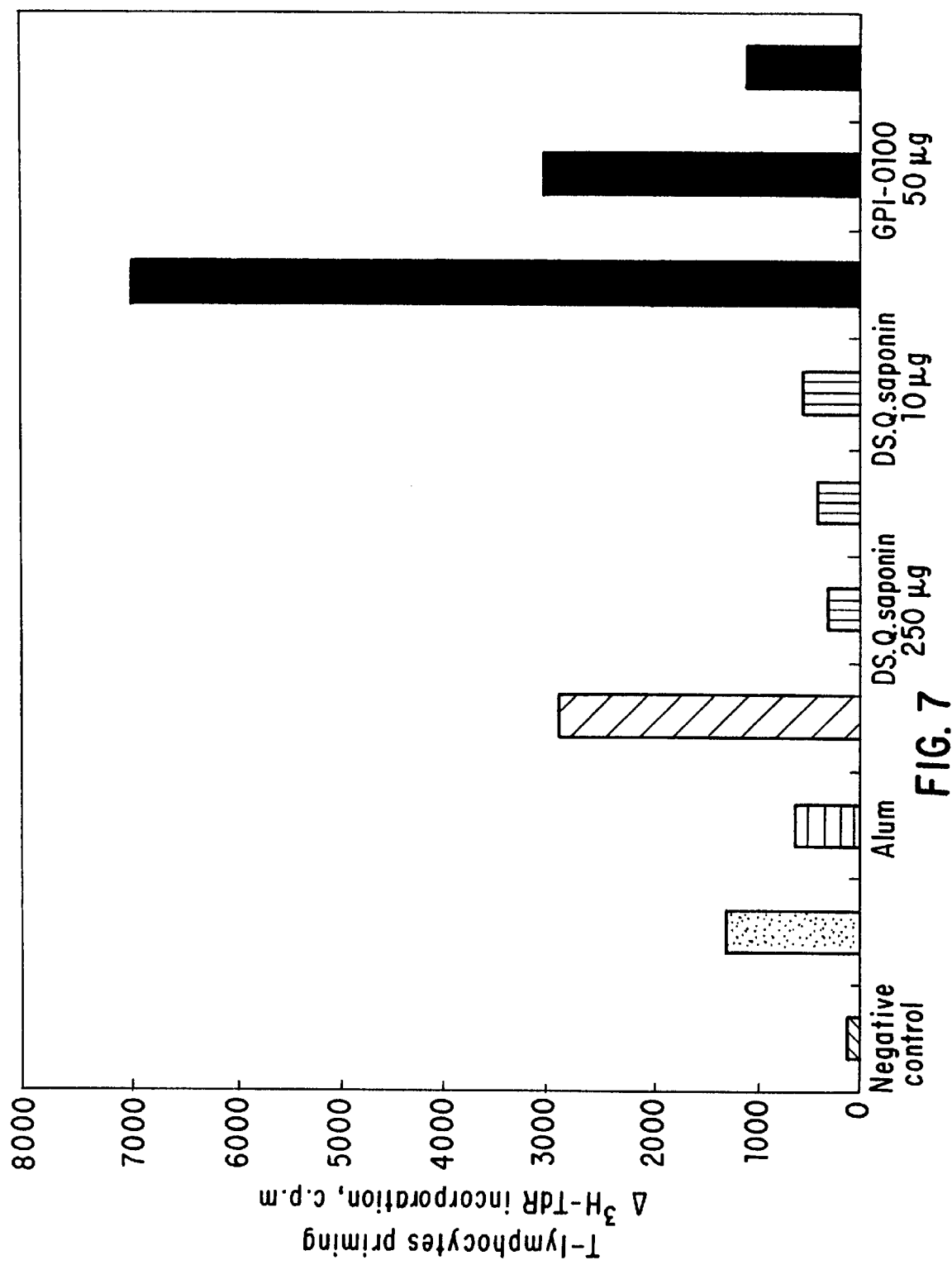
FIG. 7 demonstrates the comparison of the in vitro proliferative responses induced in T-lymphocytes isolated from mice immunized twice with OVA alone, or in the presence of alum, quillaja saponin, differing doses of desacylated quillajasaponin, and quillajasaponin-lipophile conjugate of the present invention (GPI-0100). The degree of priming was determined by stimulating the spleenocytes with either 2 or 10 $\mu$g of OVA and measuring the incremental changes in $^3$H-thymidine incorporation ($\Delta$ $^3$H-TDR incorporation, c.p.m.).

The adjuvant effect on T-cell immunity is measured by a cell proliferation assay according to the following protocol. Six to eight week old female C57BL/6 mice are immunized twice subcutaneously with the following formulation: 20 μg OVA (Sigma) and an adjuvant of the present invention or desacylated quillajasaponins (at doses ranging from 10–250 μg) or quillajasaponins (at a dose of 10 μg) in 200 μl PBS. The two immunizations are given at two week intervals. Control mice are injected with either PBS or PBS with OVA, plus 200 μg of aluminum hydroxide. Two weeks after the second immunization, the spleens are removed and disrupted by extruding through a nylon mesh. The cells are washed and resuspended in RPMI 1640 medium with 10% heat-inactivated fetal calf serum, 100 μg/ml streptomycin, 100 μg/ml penicillin, 10 μg/ml gentamycin, 2 mM L-glutamine, and 2×10–5 M 2-mercaptoethanol. Two×$10^5$ spleen cells are dispensed in 100 μl volumes into microtiter plate wells, and cultured in triplicate with either medium alone (for use as background), 3 μg/ml Concavalin A, 2 μg/ml of OVA or 10 μg/ml of OVA. After 72 h. in culture, the cells are pulsed with 1 μCi of tritiated thymidine ($^3$H-thymidine, Amersham International) for 16 h. and harvested using a Skatron (Sterling, VA) semi-automated harvester. The amount of label that is incorporated into cellular DNA is determined by liquid scintillation counting. Cell proliferation is expressed as the differential (Δ cpm) in $^3$H-thymidine incorporated between the spleenocytes stimulated with either 2 or 10 μg of OVA in vitro. As determined from the $^3$H-thymidine incorporation in the presence of OVA, T-lymphocytes from mice immunized with OVA plus quillajasaponins show a proliferative response that is significantly higher than that observed with alum. T-cells from mice immunized with OVA and different doses of desacylated quillajasaponins showed a proliferative response that was lower than that observed with alum. T-lymphocytes from mice immunized with OVA plus 50 or 250 μg of saponin conjugate, (dodecylamine conjugated to desacylated quillaja saponin) showed an in vitro proliferative response (Δ c.p.m.) that was similar to or considerably higher than that observed with quillajasaponins (FIG. 7).

EXAMPLE 10

Addition of Biotin to the Carboxyl Group of Glucuronic Acid

A $C_2$–$C_6$ aliphatic diamine is added to the carboxyl group of the glucuronic acid residue of saponins from gypsophila, saponaria, or the desacylated quillajasaponins using the carbodiimide method described in Example 2. Addition of the biotin group is achieved by linking an active ester derivative (S-NHS) of biotin (Pierce) to the free amino group of the $C_2$–$C_6$ aliphatic diamine derivative of the saponin.

EXAMPLE 11

Testing for Binding of Biotinylated Saponins to T-cells

Lymphoblasts, white blood cells, or cultured cells, are incubated in PBS at 37° C. with biotinylated saponin, with or without Na cyanoborohydride. After incubation, the cells are washed with PBS containing BSA, and collected by centrifugation. To the washed and re-suspended cells, a FITC-conjugated avidin or strepavidin (xx mg/ml) is added and the mixture is incubated for xx min. at xx° C. The cells are washed with PBS containing 10% fetal calf serum, and the samples are analyzed by fluorescence microscopy or by flow cytometry. Cells incubated with biotinylated saponin without cyanoborohydride are used to provide a background measure. Cells incubated in the presence of cyanoborohydride provide a measure of the T-cells with CD28 cell-surface-receptors which are capable of binding imine-forming saponins (including those that are biotinylated). These cells are susceptible to co-stimulation by B7.1 and thus to activation.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.
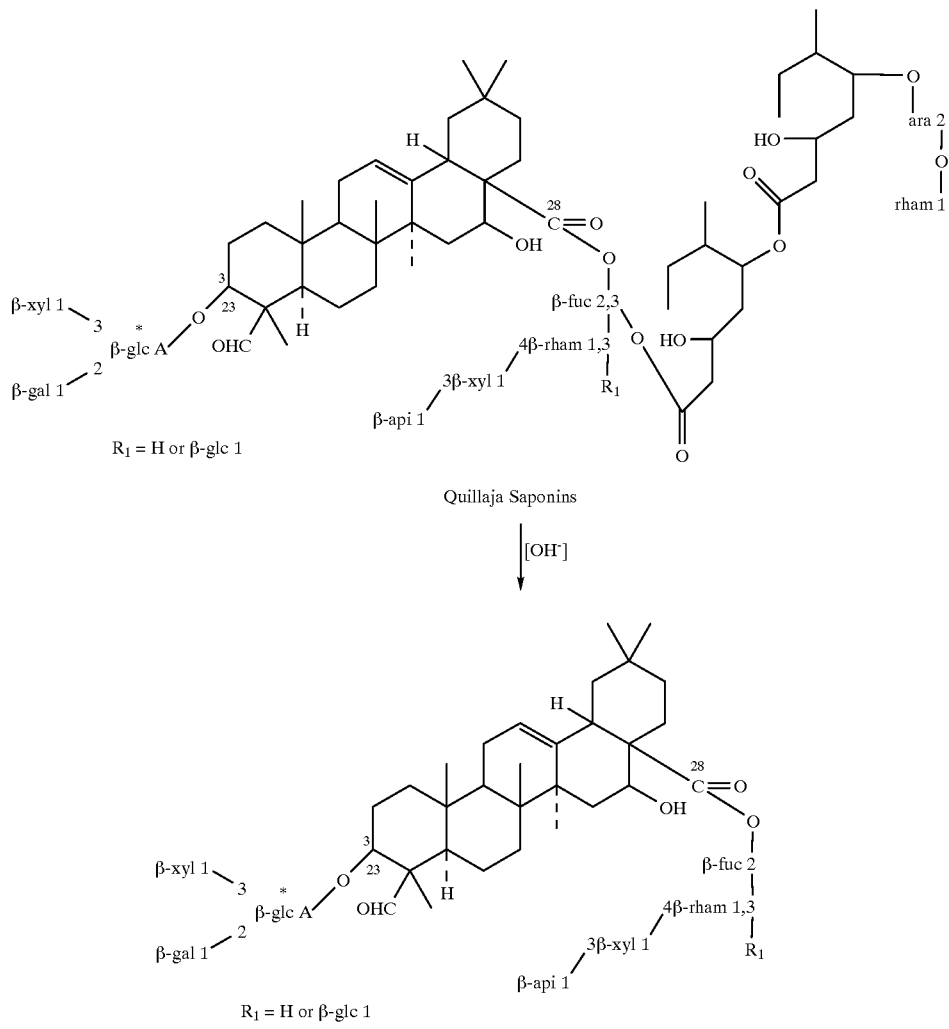
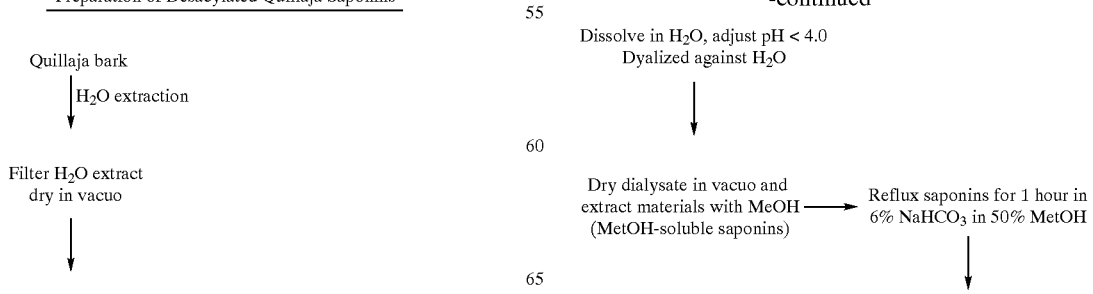

-continued
Desacylsaponins DS-1 and DS-2 plus free acyl groups ← Neutralize w/ Dowex 50W-X8, filter and evaporate in vacuo
↓
Silica gel chromatography —Elute w/ CHCl$_3$-MeOH-AcOH-H$_2$O→ DS-1
DS-2
Acyl groups and sugars (discard)
Scheme 4
Synthesis of hydrophobic-hydrophilic side-chain
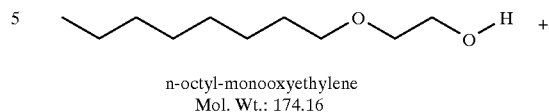
n-octyl-monooxyethylene
Mol. Wt.: 174.16
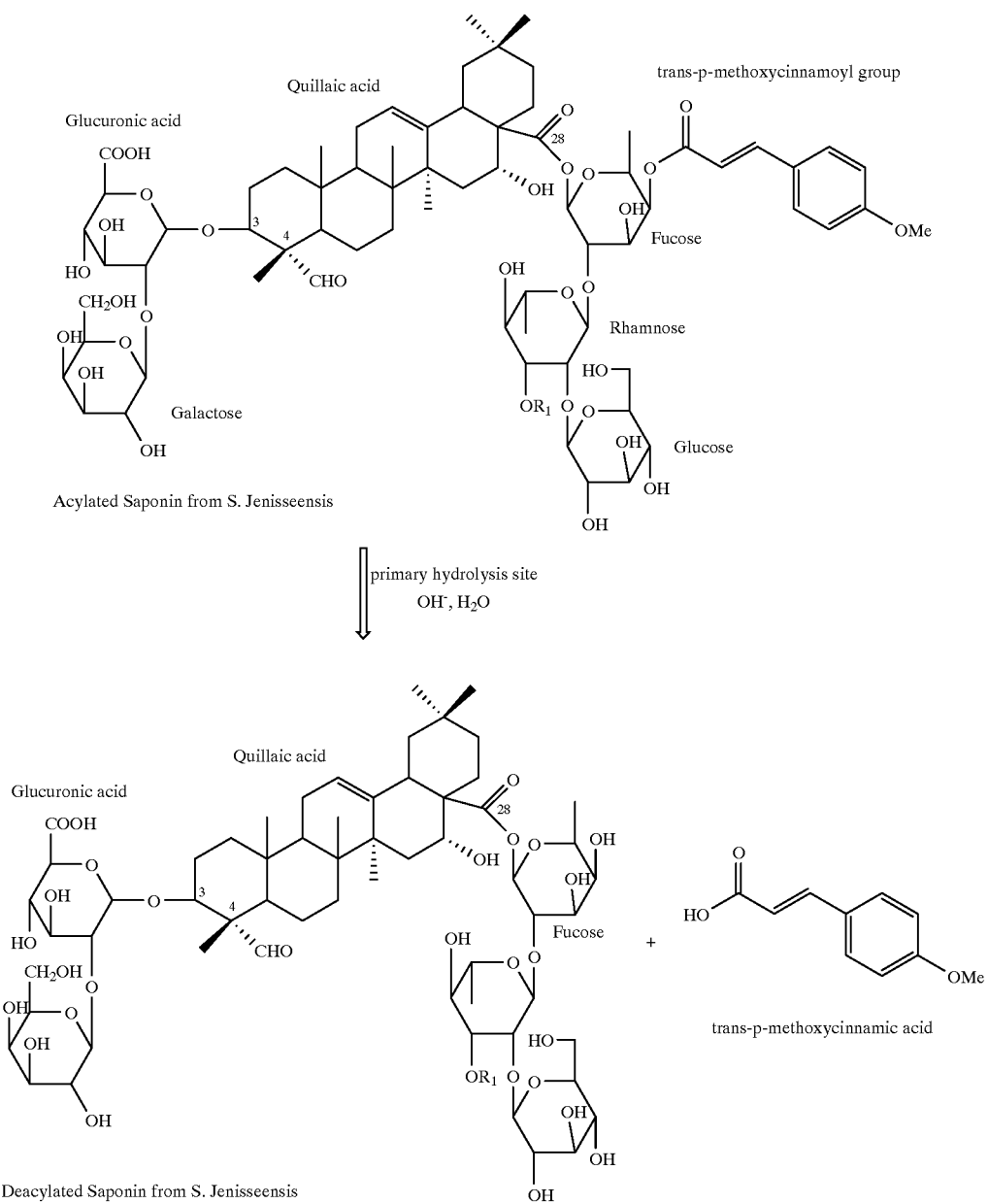

37
-continued
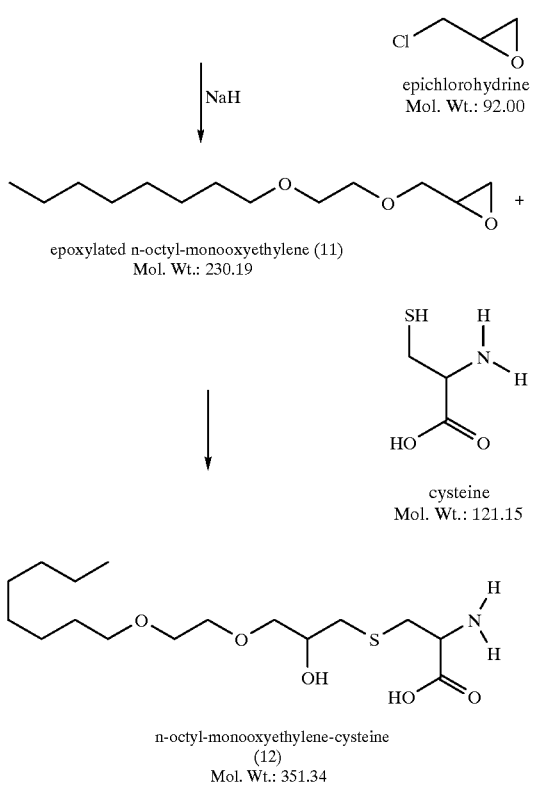
Scheme 5
Activation of Glucuronic acid in DS-Quillajasaponin
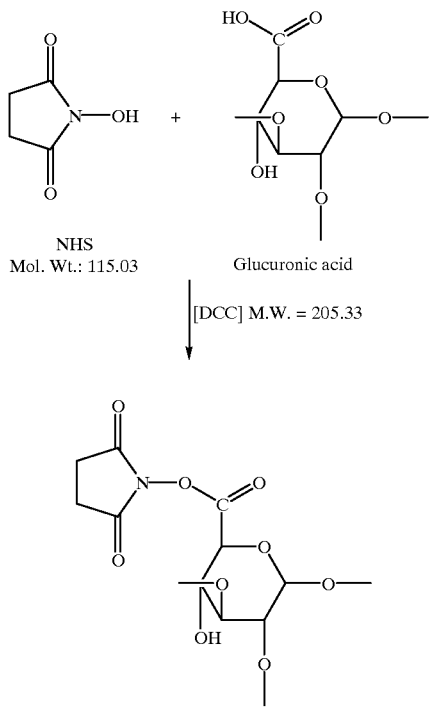
38
Scheme 6
Addition of the hydrophobic-hydrophilic side-chain to DS-saponin
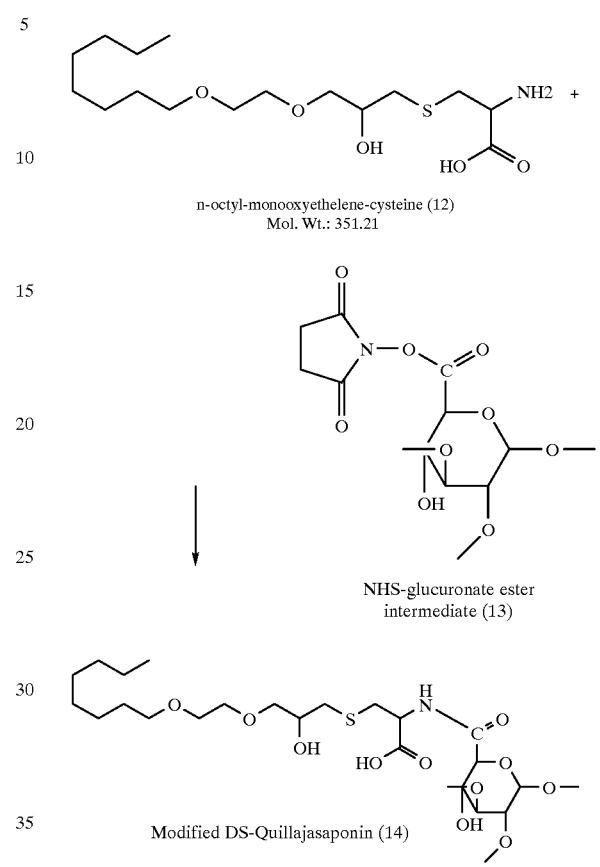

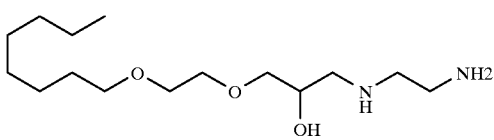

side-chain w/ ethylenediamine
Mol. Wt.: 332.30

Scheme 8
Addition of the hydrophobic-hydrophilic side-chain to DS-saponin

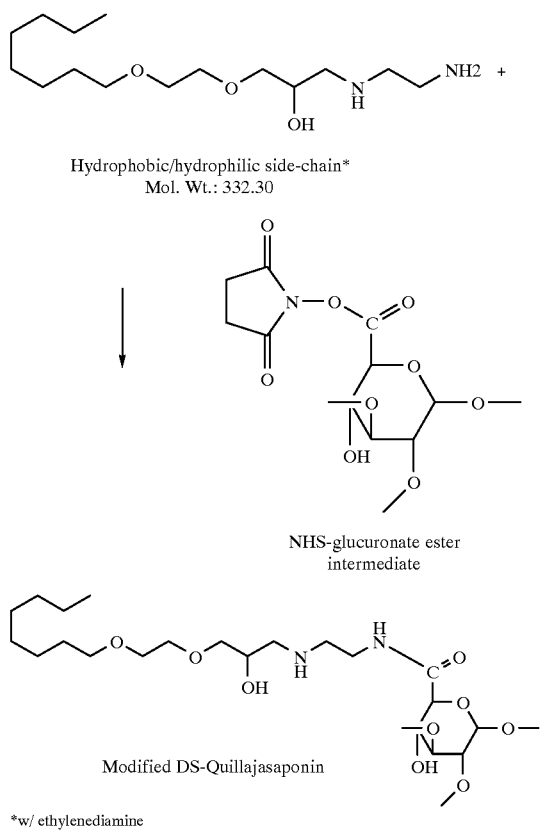

What is claimed is:

1. A triterpene saponin-lipophile conjugate, comprising
a nonacylated or desacylated triterpene saponin that includes a 3-glucuronic acid residue; and
a lipophilic moiety;
wherein said saponin and said lipophilic moiety are covalently attached to one another, either directly or through a linker group, and wherein said direct attachment or attachment to said linker occurs through a covalent bond between the carboxyl carbon of said 3-glucuronic acid residue, and a suitable functional group on the lipophilic residue or linker group.

2. The saponin-lipophile conjugate of claim 1, wherein said triterpene saponin (a) has a triterpene aglycone core structure with branched sugar chains attached to positions 3 and 28, and an aldehyde group linked or attached to position 4; and (b) is either originally non-acylated, or require removal of an acyl or acyloil group that is bound to a saccharide at the 28-position of the triterpene aglycone.

3. The saponin-lipophile conjugate of claim 1, wherein said triterpene saponin has a quillaic acid or gypsogenin core structure.

4. The saponin-lipophile conjugate of claim 1, wherein said desacylsaponin or nonacylated saponin is selected from the group consisting of Quillaja desacylsaponin, S. jenisseensis desacylsaponin Gypsophila saponin, Saponaria saponin Acanthophyllum saponin and lucyoside P saponin.

5. The saponin-lipophile conjugate of claim 1, wherein said lipophilic moiety comprises one or more residues of a fatty acid, terpenoid, aliphatic amine, aliphatic alcohol, aliphatic mercapton mono- or poly- $C_2$–$C_4$ alkyleneoxy derivative of a fatty acid, mono- or poly- $C_2$–$C_4$ alkyleneoxy derivative of a fatty alcohol, glycosyl-fatty acid, glycolipid, phospholipid or a mono-, or di-acylglycerol.

6. The saponin-lipophile conjugate of claim 5, wherein said lipophilic moiety comprises the residues of one or more $C_6$–$C_{20}$ fatty acid.

7. The saponin-lipophile conjugate of claim 6, wherein said lipophilic moiety is the residue of a $C_{14}$–$C_{24}$ fatty acid.

8. The saponin-lipophile conjugate of claim 7, wherein said fatty acid is selected from the group consisting of lauric, myristic, palmitic, stearic, arachidic, behenic, lignoceric palmitoleic, oleic, linoleic, linolenic and arachidonic acid.

9. The saponin-lipophile conjugate of claim 5, wherein said lipophilic moiety comprises the residues of one or more aliphatic amines, aliphatic alcohols, or aliphatic mercaptans.

10. The saponin-lipophile conjugate of claim 9, wherein said aliphatic amines, aliphatic alcohols or aliphatic mercaptans have from 6 to 20 carbon atoms.

11. The saponin-lipophile conjugate of claim 10, wherein said lipophilic moiety is the residue of nonylamine or dodecylamine.

12. The saponin-lipophile conjugate of claim 5, wherein said lipophilic moiety is the residue of a terpenoid.

13. The saponin-lipophile conjugate of claim 12, wherein said lipophilic moiety is the residue of retinal A.

14. The saponin-lipophile conjugate of claim 5, wherein said lipophilic moiety comprises the residues of one or more phosphoglycerides, mono-acylglycerols or di-acylglycerols.

15. The saponin-lipophile conjugate of claim 5, wherein said lipophilic moiety is the residue of an glycosyl-fatty acid or a glycolipid.

16. The saponin-lipophile conjugate of claim 15, wherein said lipophilic moiety is the residue of glucosamine-ricinoleic acid.

17. The saponin-lipophile conjugate of claim 1, wherein said nonacylated or desacylated triterpene saponin is directly attached to said lipophilic moiety via a covalent bond between the 3-glucuronic acid residue of the triterpene saponin and a reactive functional group of the lipophilic residue.

18. The saponin-lipophile conjugate of claim 1, wherein said nonacylated or desacylated triterpene saponin is attached to said lipophilic residue via a bifunctional linker having a first functional group that forms a bond between the 3-glucuronic acid residue of the triterpene saponin and a second functional group that forms a bond with a reactive functional group of the lipophilic residue.

19. The saponin-lipophile conjugate of claim 1, wherein said linking group is selected from the group consisting of —NH—$CH_2$—$CH_2$—NH—, —NH—CH(COOH)—$CH_2$—NH—, —NH—$CH_2$—CH(COOH)—NH—, —NH—$CH_2$—$CH_2$—$CH_2$—NH—, —O—$(CH_2)_r$—NH—, —S—$(CH_2)_r$—NH—, —S—$(CH_2)_r$—C(O)— —NH—$CH_2$—C(O)—, —O—$CH_2$—$CH_2$—O—$CH_2$—$CH_2$—O—, —NH—NH—C(O)—$CH_2$—, —NH —$C(CH_3)_2$—C(O)—, and —NH—NH—C(O)—(CH$_2$)$_r$—C(O)NH—N=, where r, in each instance, is from 2–5.

20. The saponin-lipophile conjugate of claim 1, wherein said conjugate is represented by Formula II:

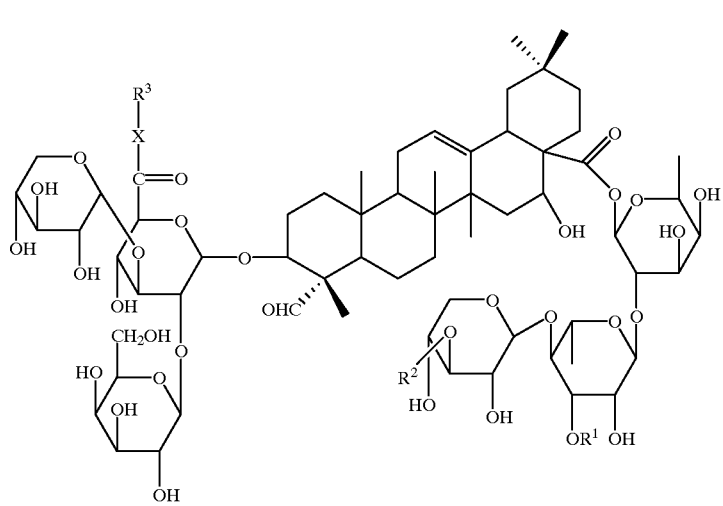

or a pharmaceutically acceptable salt thereof; wherein
R$^1$ is glucose or hydrogen; R$^2$ is apiose or xylose; X is S, O, NH or a linking group; and R$^3$ is a lipophilic moiety.

21. The saponin-lipophile conjugate of claim 1, wherein said conjugate is represented by Formula IV:

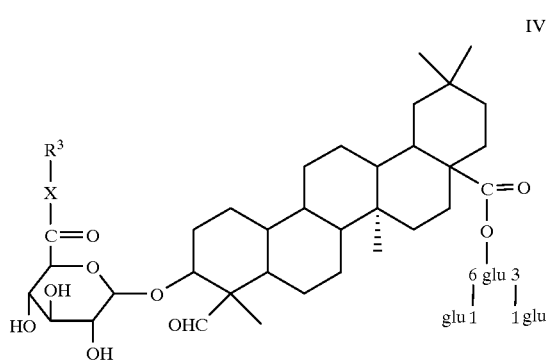

or a pharmaceutically acceptable salt thereof; wherein
X is S, O, NH or a linking group; and
R$^3$ is a lipophilic moiety.

22. The saponin-lipophile conjugate of claim 20, wherein X is a linking group, and said linking group is a bifunctional molecule.

23. The saponin-lipophile conjugate of claim 20, wherein X is NH.

24. The saponin-lipophile conjugate of claim 20, wherein X is O.

25. The saponin-lipophile conjugate of claim 20, wherein X is S.

26. The saponin-lipophile conjugate of claim 20, wherein X is a lipophilic moiety selected from the group consisting of fatty acid, terpenoid, aliphatic amine, aliphatic alcohol, polyethylene glycol, glycosyl-fatty acid, glycolipid, phospholipid and mono-acylglycerol and di-acylglycerol.

27. A pharmaceutical composition, comprising
one or more saponin-lipophile conjugates of claim 1, and
a pharmaceutically acceptable carrier or diluent.

28. The pharmaceutical composition of claim 27, further comprising an antigen.

29. A vaccine, comprising:
(a) one or more saponin-lipophile conjugates of claim 1;
(b) an immunologically effective amount of an antigen; and
(c) a pharmaceutically acceptable carrier or diluent.

30. A method of enhancing an immune response in an animal, comprising administering to an animal in need of such enhancing a composition of claim 27 in an amount effective to enhance the immune response of said animal.

31. A method of potentiating an immune response to an antigen in an animal, comprising administering a composition of claim 28 in an effective amount to potentiate the immune response of said animal to said antigen.

32. A method of vaccinating an animal, comprising administering a vaccine of claim 29 to said animal.

33. The saponin-lipophile conjugate of claim 1, wherein said conjugate is represented by Formula III:

III

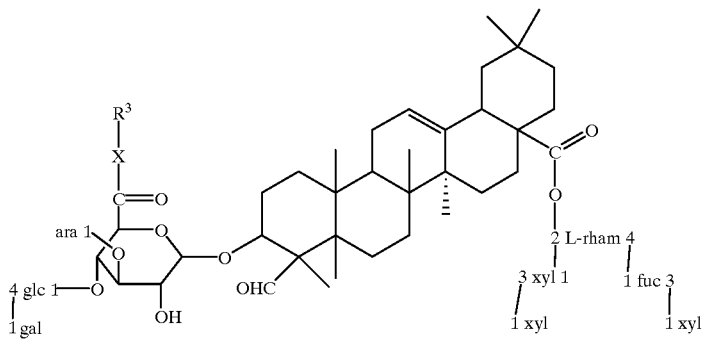

or a pharmaceutically acceptable salt thereof; wherein

X is S, O, NH or a linking group; and $R^3$ is a lipophilic moiety.

34. The saponin-lipophile conjugate of claim 33, wherein the combination of —X—$R^3$ is a residue of a compound selected from the group consisting of fatty acid, terpenoid, aliphatic amine aliphatic alcohol, aliphatic mercaptan, polyethylene glycol, glycosyl-fatty acid, glycolipid, phospholipid and mono-acylglycerol and di-acylglycerol.

35. The saponin-lipophile conjugate of claim 21, wherein the combination of —X—$R^3$ is a residue of a compound selected from the group consisting of fatty acid, terpenoid, aliphatic amine, aliphatic alcohol, aliphatic mercaptan, polyethylene glycol, glycosyl-fatty acid, glycolipid, phospholipid, mono-acylglycerol and di-acylglycerol.

36. The saponin-lipophile conjugate of claim 20, wherein the combination of —X—$R^3$ is a residue of a compound selected from the group consisting of fatty acid, terpenoid, aliphatic amine, aliphatic alcohol, aliphatic mercaptan, mono- or poly- $C_2$–$C_4$ alkyleneoxy derivative of a fatty acid, mono- or poly- $C_2$–$C_4$ alkyleneoxy derivative of a fatty alcohol, glycosyl-fatty acid, glycolipid, phospholipid and a mono-, or di-acylglycerol.

37. The saponin-lipophile conjugate of claim 4, wherein said nonacylated or desacylated triterpene saponin is Quillaja desacylsaponin.

38. The saponin-lipophile conjugate of claim 37, wherein said lipophilic moiety comprises one or more residues of a fatty acid, terpenoid, aliphatic amine, aliphatic alcohol, aliphatic mercaptan, mono- or poly- $C_2$–$C_4$ alkyleneoxy derivative of a fatty acid, mono- or poly- $C_2$–$C_4$ alkyleneoxy derivative of a fatty alcohol, glycosyl-fatty acid, glycolipid, phospholipid and a mono-, or di-acylglycerol.

39. The saponin-lipophile conjugate of claim 38, wherein said lipophilic moiety comprises a residue of one or more $C_6$–$C_{20}$ fatty acids.

40. The saponin-lipophile conjugate of claim 39, wherein said lipophilic moiety is a residue of a $C_{14}$–$C_{24}$ fatty acid.

41. The saponin-lipophile conjugate of claim 40, wherein said fatty acid is selected from the group consisting of lauric, myristic, palmitic, stearic, arachidic, behenic, lignoceric, palmitoleic, oleic, linoleic, linolenic and arachidonic acid.

42. The saponin-lipophile conjugate of claim 38, wherein said lipophilic moiety comprises a residue of one or more aliphatic amines, aliphatic alcohols, or aliphatic mercaptans.

43. The saponin-lipophile conjugate of claim 42, wherein said aliphatic amines, aliphatic alcohols or aliphatic mercaptans have from 6 to 20 carbon atoms.

44. The saponin-lipophile conjugate of claim 43, wherein X is NH, and $R^3$ is nonyl or dodecyl.

45. The saponin-lipophile conjugate of claim 38, wherein said lipophilic moiety is the residue of a terpenoid.

46. The saponin-lipophile conjugate of claim 45, wherein said lipophilic moiety is the residue of retinal A.

47. The saponin-lipophile conjugate of claim 38, wherein said lipophilic moiety comprises the residues of one or more phosphoglycerides, mono-acylglycerols or di-acylglycerols.

48. The saponin-lipophile conjugate of claim 38, wherein said lipophilic moiety is the residue of an glycosyl-fatty acid or a glycolipid.

49. The saponin-lipophile conjugate of claim 38, wherein said lipophilic moiety is the residue of glucosamine-ricinoleic acid.

50. The saponin-lipophile conjugate of claim 20, wherein X is S, O, NH or a linking group selected from the group consisting of —NH—$CH_2$—$CH_2$—NH—, —NH—CH(COOH)—$CH_2$—NH—, —NH—$CH_2$—CH(COOH)—NH—, —NH—$CH_2$—$CH_2$—$CH_2$—NH—, —O—$(CH_2)_r$—NH—, —S—$(CH_2)_r$—NH—, —S—$(CH_2)_r$—C(O)— —NH—$CH_2$—C(O)—, —O—$CH_2$—$CH_2$—O—$CH_2$—$CH_2$—O—, —NH—NH—C(O)—$CH_2$—, —NH—C($CH_3$)$_2$—C(O)—, and —NH—NH—C(O)—$(CH_2)_r$—C(O)—NH—N=, where r, in each instance, is from 2–5.

* * * * *